(12) United States Patent
Sabina et al.

(10) Patent No.: US 11,954,262 B2
(45) Date of Patent: *Apr. 9, 2024

(54) OVERLAY FOR INTRAORAL SCANNING SYSTEM USER INTERFACE

(71) Applicant: Align Technology, Inc., San Jose, CA (US)

(72) Inventors: Michael Sabina, Campbell, CA (US); Leon Rasovsky, Mountain View, CA (US)

(73) Assignee: Align Technology, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/826,028

(22) Filed: May 26, 2022

(65) Prior Publication Data

US 2022/0291754 A1    Sep. 15, 2022

Related U.S. Application Data

(63) Continuation of application No. 16/795,885, filed on Feb. 20, 2020, now Pat. No. 11,392,210, which is a
(Continued)

(51) Int. Cl.
*G06F 3/01* (2006.01)
*A61C 5/77* (2017.01)
(Continued)

(52) U.S. Cl.
CPC ............... *G06F 3/017* (2013.01); *A61C 5/77* (2017.02); *A61C 9/0053* (2013.01);
(Continued)

(58) Field of Classification Search
CPC .................................................. A61C 9/0053
See application file for complete search history.

(56) References Cited

U.S. PATENT DOCUMENTS

| 6,099,314 A | 8/2000 | Kopelman et al. |
| 6,334,772 B1 | 1/2002 | Taub et al. |

(Continued)

FOREIGN PATENT DOCUMENTS

CN    104038659 A    9/2014

OTHER PUBLICATIONS 3M (3M ESPE Lava Chairside Oral Scanner User Guide Version 3.0; published 2010) (Year: 2010).*

*Primary Examiner* — Tan H Tran
(74) *Attorney, Agent, or Firm* — Lowenstein Sandler, LLP

(57) ABSTRACT

A scanning system comprises an intraoral scanner to capture scan data of a dental site and a computing device to generate a 3D rendering of the dental site. The scanner comprises one or more input devices configured to provide manual interaction with the computing device, where: a first activation of the input device(s) causes the scanning system to enter the scan mode, wherein the 3D rendering has a first visualization during the scan mode; and a second activation of the input device(s) causes the scanning system to enter an overlay mode, wherein the 3D rendering has a second visualization during the overlay mode, wherein the computing device is to present a menu comprising menu options on the display while the scanning system is in the overlay mode, and wherein the scanner is usable to select among the presented menu options.

29 Claims, 10 Drawing Sheets

Related U.S. Application Data continuation of application No. 16/129,641, filed on Sep. 12, 2018, now Pat. No. 10,599,227, which is a continuation of application No. 14/641,188, filed on Mar. 6, 2015, now Pat. No. 10,108,269.

(51) Int. Cl.
*A61C 9/00* (2006.01)
*A61C 13/00* (2006.01)
*G06F 3/0346* (2013.01)
*G06F 3/04883* (2022.01)
*G16H 20/40* (2018.01)

(52) U.S. Cl.
CPC ........ *A61C 13/0004* (2013.01); *G06F 3/0346* (2013.01); *G06F 3/04883* (2013.01); *G16H 20/40* (2018.01)

(56) References Cited

U.S. PATENT DOCUMENTS

| | | |
|---|---|---|
| 6,334,853 B1 | 1/2002 | Kopelman et al. |
| 6,463,344 B1 | 10/2002 | Pavlovskaia et al. |
| 6,542,249 B1 | 4/2003 | Kofman et al. |
| 6,633,789 B1 | 10/2003 | Nikolskiy et al. |
| 6,664,986 B1 | 12/2003 | Kopelman et al. |
| 6,697,164 B1 | 2/2004 | Babayoff et al. |
| 6,845,175 B2 | 1/2005 | Kopelman et al. |
| 6,979,196 B2 | 12/2005 | Nikolskiy et al. |
| 7,030,383 B2 | 4/2006 | Babayoff et al. |
| 7,202,466 B2 | 4/2007 | Babayoff et al. |
| 7,255,558 B2 | 8/2007 | Babayoff et al. |
| 7,286,954 B2 | 10/2007 | Kopelman et al. |
| 7,319,529 B2 | 1/2008 | Babayoff |
| 7,373,286 B2 | 5/2008 | Nikolskiy et al. |
| 7,507,088 B2 | 3/2009 | Taub et al. |
| 7,545,372 B2 | 6/2009 | Kopelman et al. |
| 7,698,068 B2 | 4/2010 | Babayoff |
| 7,916,911 B2 | 3/2011 | Kaza et al. |
| 8,108,189 B2 | 1/2012 | Chelnokov et al. |
| 8,244,028 B2 | 8/2012 | Kuo et al. |
| 8,587,582 B2 | 11/2013 | Matov et al. |
| 8,948,482 B2 | 2/2015 | Levin |
| D742,518 S | 11/2015 | Barak et al. |
| 9,192,305 B2 | 11/2015 | Levin |
| 9,261,356 B2 | 2/2016 | Lampert et al. |
| 9,261,358 B2 | 2/2016 | Atiya et al. |
| 9,299,192 B2 | 3/2016 | Kopelman |
| D760,901 S | 7/2016 | Barak et al. |
| 9,393,087 B2 | 7/2016 | Moalem |
| 9,408,679 B2 | 8/2016 | Kopelman |
| 9,431,887 B2 | 8/2016 | Boltanski |
| 9,439,568 B2 | 9/2016 | Atiya et al. |
| 9,451,873 B1 | 9/2016 | Kopelman et al. |
| D768,861 S | 10/2016 | Barak et al. |
| D771,817 S | 11/2016 | Barak et al. |
| 9,491,863 B2 | 11/2016 | Boltanski |
| D774,193 S | 12/2016 | Makmel et al. |
| 9,510,757 B2 | 12/2016 | Kopelman et al. |
| 9,660,418 B2 | 5/2017 | Atiya et al. |
| 9,668,829 B2 | 6/2017 | Kopelman |
| 9,675,430 B2 | 6/2017 | Verker et al. |
| 9,693,839 B2 | 7/2017 | Atiya et al. |
| 9,717,402 B2 | 8/2017 | Lampert et al. |
| 9,724,177 B2 | 8/2017 | Levin |
| 9,844,426 B2 | 12/2017 | Atiya et al. |
| 10,076,389 B2 | 9/2018 | Wu et al. |
| 10,098,714 B2 | 10/2018 | Kuo |
| 10,108,269 B2 | 10/2018 | Sabina et al. |
| 10,111,581 B2 | 10/2018 | Makmel |
| 10,111,714 B2 | 10/2018 | Kopelman et al. |
| 10,123,706 B2 | 11/2018 | Elbaz et al. |
| 10,136,972 B2 | 11/2018 | Sabina et al. |
| 10,380,212 B2 | 8/2019 | Elbaz et al. |
| 10,390,913 B2 | 8/2019 | Sabina et al. |
| 10,453,269 B2 | 10/2019 | Furst |
| 10,456,043 B2 | 10/2019 | Atiya et al. |
| 10,499,793 B2 | 12/2019 | Ozerov et al. |
| 10,504,386 B2 | 12/2019 | Levin et al. |
| 10,507,087 B2 | 12/2019 | Elbaz et al. |
| 10,517,482 B2 | 12/2019 | Sato et al. |
| 10,695,150 B2 | 6/2020 | Kopelman et al. |
| 10,708,574 B2 | 7/2020 | Furst et al. |
| 10,772,506 B2 | 9/2020 | Atiya et al. |
| 10,813,727 B2 | 10/2020 | Sabina et al. |
| 10,888,399 B2 | 1/2021 | Kopelman et al. |
| 10,952,816 B2 | 3/2021 | Kopelman |
| 10,980,613 B2 | 4/2021 | Shanjani et al. |
| 11,013,581 B2 | 5/2021 | Sabina et al. |
| D925,739 S | 7/2021 | Shalev et al. |
| 11,096,765 B2 | 8/2021 | Atiya et al. |
| 11,238,586 B2 | 2/2022 | Minchenkov et al. |
| 11,367,192 B2 | 6/2022 | Kopelman et al. |
| 2007/0171220 A1* | 7/2007 | Kriveshko ................ G06T 7/30 345/419 |
| 2012/0249595 A1 | 10/2012 | Feinstein |
| 2013/0257718 A1* | 10/2013 | Ojelund ............... A61B 5/0088 345/156 |
| 2015/0056576 A1* | 2/2015 | Nikolskiy .......... A61C 13/0004 433/214 |
| 2019/0029784 A1 | 1/2019 | Moalem et al. |
| 2019/0265946 A1* | 8/2019 | Bae ........................ G06F 3/038 |
| 2019/0290408 A1* | 9/2019 | Fisker ................... A61C 11/00 |
| 2019/0388193 A1 | 12/2019 | Saphier et al. |
| 2020/0281702 A1 | 9/2020 | Kopelman et al. |
| 2020/0315434 A1 | 10/2020 | Kopelman et al. |
| 2020/0349705 A1 | 11/2020 | Minchenkov et al. |
| 2020/0404243 A1 | 12/2020 | Saphier et al. |
| 2021/0030503 A1 | 2/2021 | Shalev et al. |
| 2021/0059796 A1 | 3/2021 | Weiss et al. |
| 2021/0068773 A1 | 3/2021 | Moshe et al. |
| 2021/0121049 A1 | 4/2021 | Rudnitsky et al. |
| 2021/0128281 A1 | 5/2021 | Peleg |
| 2021/0137653 A1 | 5/2021 | Saphier et al. |
| 2021/0196152 A1 | 7/2021 | Saphier et al. |

\* cited by examiner

OVERLAY FOR INTRAORAL SCANNING SYSTEM USER INTERFACE

RELATED APPLICATION

This application is a continuation application of U.S. patent application Ser. No. 16/795,885, filed Feb. 20, 2020, which is a continuation application of U.S. patent application Ser. No. 16/129,641, filed Sep. 12, 2018, which is a continuation application of U.S. patent application Ser. No. 14/641,188, filed Mar. 6, 2015, all of which are hereby incorporated by reference herein.

TECHNICAL FIELD

Embodiments of the present invention relate to the field of intraoral scanning and, in particular, to an intraoral scanner with touch sensitive input.

BACKGROUND

In prosthodontic procedures designed to implant a dental prosthesis in the oral cavity, the dental site at which the prosthesis is to be implanted in many cases should be measured accurately and studied carefully, so that a prosthesis such as a crown, denture or bridge, for example, can be properly designed and dimensioned to fit in place. A good fit enables mechanical stresses to be properly transmitted between the prosthesis and the jaw, and to prevent infection of the gums via the interface between the prosthesis and the dental site, for example.

Some procedures also call for removable prosthetics to be fabricated to replace one or more missing teeth, such as a partial or full denture, in which case the surface contours of the areas where the teeth are missing need to be reproduced accurately so that the resulting prosthetic fits over the edentulous region with even pressure on the soft tissues.

In some practices, the dental site is prepared by a dental practitioner, and a positive physical model of the dental site is constructed using known methods. Alternatively, the dental site may be scanned to provide 3D data of the dental site. In either case, the virtual or real model of the dental site is sent to the dental lab, which manufactures the prosthesis based on the model. However, if the model is deficient or undefined in certain areas, or if the preparation was not optimally configured for receiving the prosthesis, the design of the prosthesis may be less than optimal. For example, if the insertion path implied by the preparation for a closely-fitting coping would result in the prosthesis colliding with adjacent teeth, the coping geometry has to be altered to avoid the collision, which may result in the coping design being less optimal. Further, if the area of the preparation containing a finish line lacks definition, it may not be possible to properly determine the finish line and thus the lower edge of the coping may not be properly designed. Indeed, in some circumstances, the model is rejected and the dental practitioner then re-scans the dental site, or reworks the preparation, so that a suitable prosthesis may be produced.

In orthodontic procedures it can be important to provide a model of one or both jaws. Where such orthodontic procedures are designed virtually, a virtual model of the oral cavity is also beneficial. Such a virtual model may be obtained by scanning the oral cavity directly, or by producing a physical model of the dentition, and then scanning the model with a suitable scanner.

Thus, in both prosthodontic and orthodontic procedures, obtaining a three-dimensional (3D) model of a dental site in the oral cavity is an initial procedure that is performed. When the 3D model is a virtual model, the more complete and accurate the scans of the dental site are, the higher the quality of the virtual model, and thus the greater the ability to design an optimal prosthesis or orthodontic treatment appliance(s).

BRIEF DESCRIPTION OF THE DRAWINGS

Embodiments of the present invention are illustrated by way of example, and not by way of limitation, in the figures of the accompanying drawings.

DETAILED DESCRIPTION

Figure 1:
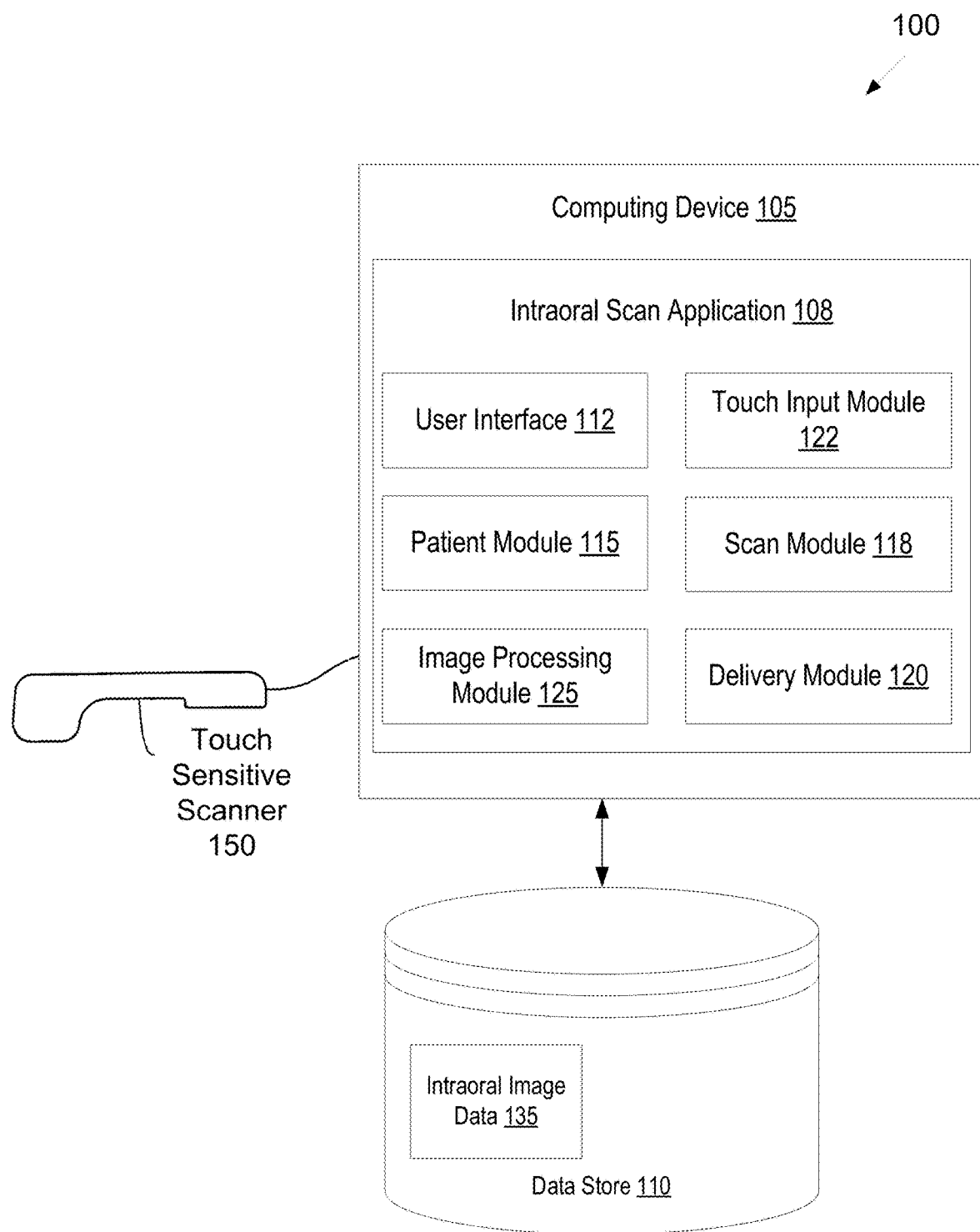
FIG. 1 illustrates one embodiment of a system for performing intraoral scanning and generating a virtual three dimensional model of a dental site.

Described herein is a method and apparatus for improving medical scanning using a touch sensitive medical scanning device, such as a touch sensitive intraoral scanner. During a scan session, a user (e.g., a dental practitioner) of a scanner may generate multiple different images (also referred to as scans or medical images) of a dental site, model of a dental site, or other object. The images may be discrete images (e.g., point-and-shoot images) or frames from a video (e.g., a continuous scan). Existing medical scanning solutions frequently involve the user holding the scanner to engage the patient for scanning, disengaging from the patient to address a medical scan application executing on a computing device, then reengaging with the patient to continue the scanning process, again disengaging from the patient to address the medical scan application, and repeating until completion of a scanning session. Such processes can be quite cumbersome and inefficient. Moreover, medical scanning devices generally lack the ability to both generate medical images and then manipulate those medical images or representations thereof on a display of a computing device.

Embodiments of the present invention enable a user to perform operations (such as to control or navigate a user interface and/or to manipulate medical images or a representation generated from medical images) while still engaged with a patient that in previous systems could only be performed by disengaging from the patient and interacting with a computing device running an intraoral scan application. The ability to perform such operations while still engaged with the patient can improve the efficiency of a workflow for scanning a patient.

In one embodiment, a computing device executing a medical scan application receives a touch input from a touch sensitive medical scanning device during a medical scan session. The medical scanning device may be, for example, an intraoral scanner that includes a touch sensor (e.g., a touch pad). The computing device determines whether the touch input is a hold gesture or a swipe gesture. The computing device then performs a first function or operation to control a user interface of the medical scan application if the touch input is a hold gesture and a second function or operation to control the user interface of the medical scan application if the touch input is a swipe gesture. Examples of functions that may be performed include activating a gyroscope in the medical scanning device, using data from the gyroscope to control an orientation of a virtual 3D model (e.g., if a hold gesture is detected) and proceeding to next or previous scan segments (e.g., if a swipe gesture is detected). The functions or operations performed responsive to the hold or swipe gestures may be functions that traditionally are performed responsive to a user using a keyboard, mouse and/or touch screen of the computing device. By providing touch sensors in the medical scanning device and a medical scan application that can respond to touch input from such touch sensors, embodiments improve the efficiency of performing medical scans.

In one embodiment, a medical scanning device includes an image sensor, a communication module and a touch sensor. The image sensor generates medical images of a patient and the communication module transmits those medical images to a computing device, which may then display the medical images or a representation of the patient generated from the medical images (e.g., a 3D virtual model of a dental site of the patient). The touch sensor is then activated (e.g., by a button push combination of one or more buttons), and a user then uses the touch sensor to manipulate the medical images or the representation generated from the medical images. Thus, the same medical scanning device may be used both for generation of the medical images and manipulation of the medical images and a user interface that receives and operates on the medical images.

Embodiments described herein are discussed with reference to intraoral scanners, intraoral images, intraoral scan sessions, intraoral scan applications, and so forth. However, it should be understood that embodiments also apply to other types of scanners than intraoral scanners. Embodiments may apply to any type of medical scanning device, such as those that take multiple images and stitch these images together to form a combined image or virtual model. For example, embodiments may apply to desktop model scanners, computed tomography (CT) scanners, and so forth. Embodiments may also apply to ultrasound devices that include ultrasound transceivers, x-ray devices that include an x-ray emitter and/or an x-ray detector, and other devices. Additionally, it should be understood that the intraoral scanners or other scanners may be used to scan objects other than dental sites in an oral cavity. For example, embodiments may apply to scans performed on physical models of a dental site or any other object. Accordingly, embodiments describing intraoral images should be understood as being generally applicable to any types of images generated by a scanner, embodiments describing intraoral scan sessions should be understood as being applicable to scan sessions for any type of object, embodiments describing intraoral scan applications should be understood as being applicable to medical scan applications, and embodiments describing intraoral scanners should be understood as being generally applicable to many types of scanners.

FIG. 1 illustrates one embodiment of a system 100 for performing intraoral scanning and/or generating a virtual three dimensional model of a dental site. In one embodiment, system 100 carries out one or more operations below described in methods 300 and 350. System 100 includes a computing device 105 that may be coupled to a touch sensitive scanner 150 and/or a data store 110.

Computing device 105 may include a processing device, memory, secondary storage, one or more input devices (e.g., such as a keyboard, mouse, tablet, touch screen, and so on), one or more output devices (e.g., a display, a printer, etc.), and/or other hardware components. Computing device 105 may be connected to a data store 110 either directly or via a network. The network may be a local area network (LAN), a public wide area network (WAN) (e.g., the Internet), a private WAN (e.g., an intranet), or a combination thereof. The computing device 105 may be integrated into the scanner 150 in some embodiments to improve performance and mobility.

Data store 110 may be an internal data store, or an external data store that is connected to computing device 105 directly or via a network. Examples of network data stores include a storage area network (SAN), a network attached storage (NAS), and a storage service provided by a cloud computing service provider. Data store 110 may include a file system, a database, or other data storage arrangement.

In some embodiments, a touch sensitive scanner 150 for obtaining three-dimensional (3D) data of a dental site in a patient's oral cavity is operatively connected to the computing device 105 via a communication module of the touch sensitive scanner 150. The computing device 105 may be connected to the touch sensitive scanner 150 directly or indirectly and via a wired or wireless connection. For example, the touch sensitive scanner 150 may include a communication module such as a network interface controller (NIC) capable of communicating via Wi-Fi, via third generation (3G) or fourth generation (4G) telecommunications protocols (e.g., global system for mobile communications (GSM), long term evolution (LTE), Wi-Max, code division multiple access (CDMA), etc.), via Bluetooth, via Zigbee, or via other wireless protocols. Alternatively, or additionally, touch sensitive scanner 150 may include an Ethernet network interface controller (NIC), a universal serial bus (USB) port, or other wired port. The NIC or port may connect the touch sensitive scanner to the computing device 105 via a local area network (LAN). Alternatively, the touch sensitive scanner 150 may connect to a wide area network (WAN) such as the Internet, and may connect to the computing device 105 via the WAN. In an alternative embodiment, touch sensitive scanner 150 is connected directly to the computing device 105 (e.g., via a direct wired or wireless connection). In one embodiment, the computing device 105 is a component of the touch sensitive scanner 150.

Touch sensitive scanner 150 may include a probe (e.g., a hand held probe) for optically capturing three dimensional structures (e.g., by confocal focusing of an array of light beams). Touch sensitive scanner 150 additionally includes one or more touch sensors (e.g., one or more touch pads) that can receive touch input. Touch sensitive scanner 150 may also include other components such as optical components, an accelerometer, communication components, a gyroscope, processing devices, and so on. One example of a touch sensitive scanner 150 is the iTero® intraoral digital scanner manufactured by Align Technology, Inc.

The touch sensitive scanner 150 may be used to perform an intraoral scan of a patient's oral cavity. An intraoral scan application 108 running on computing device 105 may communicate with the touch sensitive scanner 150 to effectuate the intraoral scan. A result of the intraoral scan may be a sequence of intraoral images that have been discretely generated (e.g., by pressing on a "generate image" button of the scanner for each image). Alternatively, a result of the intraoral scan may be one or more videos of the patient's oral cavity. An operator may start recording the video with the touch sensitive scanner 150 at a first position in the oral cavity, move the touch sensitive scanner 150 within the oral cavity to a second position while the video is being taken, and then stop recording the video. In some embodiments, recording may start automatically as the scanner identifies teeth and/or other objects. The touch sensitive scanner 150 may transmit the discrete intraoral images or intraoral video (referred to collectively as intraoral image data 135) to the computing device 105. Computing device 105 may store the image data 135 in data store 110. Alternatively, touch sensitive scanner 150 may be connected to another system that stores the image data in data store 110, in such an embodiment, touch sensitive scanner 150 may not be directly connected to computing device 105.

According to an example, a user (e.g., a practitioner) may subject a patient to intraoral scanning. In doing so, the user may apply touch sensitive scanner 150 to one or more patient intraoral locations. The scanning may be divided into one or more segments. As an example, the segments may include a lower buccal region of the patient, a lower lingual region of the patient, a upper buccal region of the patient, an upper lingual region of the patient, one or more preparation teeth of the patient (e.g., teeth of the patient to which a dental device such as a crown or an orthodontic alignment device will be applied), one or more teeth which are contacts of preparation teeth (e.g., teeth not themselves subject to a dental device but which are located next to one or more such teeth or which interface with one or more such teeth upon mouth closure), and/or patient bite (e.g., scanning performed with closure of the patient's mouth with the intraoral scanner being directed towards an interface area of the patient's upper and lower teeth). Via such scanner application, the touch sensitive scanner 150 may provide intraoral image data (also referred to as scan data) 135 to computing device 105. The intraoral image data 135 may include 2D intraoral images and/or 3D intraoral images. Such images may be provided from the scanner to the computing device 105 in the form of one or more points (e.g., one or more pixels and/or groups of pixels). For instance, the touch sensitive scanner 150 may provide such a 3D image as one or more point clouds.

The manner in which the oral cavity of a patient is to be scanned may depend on the procedure to be applied thereto. For example, if an upper or lower denture is to be created, then a full scan of the mandibular or maxillary edentulous arches may be performed. In contrast, if a bridge is to be created, then just a portion of a total arch may be scanned which includes an edentulous region, the neighboring abutment teeth and the opposing arch and dentition. Thus, the dental practitioner may input the identity of a procedure to be performed into medical scan application 108. For this purpose, the dental practitioner may choose the procedure from a number of preset options on a drop-down menu or the like, from icons or via any other suitable graphical input interface. Alternatively, the identity of the procedure may be input in any other suitable way, for example by means of preset code, notation or any other suitable manner, medical scan application 108 having been suitably programmed to recognize the choice made by the user. In either case, the medical practitioner may generate a treatment plan that includes one or more segments that are to be scanned. A segment (or scan segment) may include a particular tooth (e.g., a preparation tooth), an upper or lower arch, a portion of an upper or lower arch, a bite, and so on.

By way of non-limiting example, dental procedures may be broadly divided into prosthodontic (restorative) and orthodontic procedures, and then further subdivided into specific forms of these procedures. Additionally, dental procedures may include identification and treatment of gum disease, sleep apnea, and intraoral conditions. The term prosthodontic procedure refers, inter alia, to any procedure involving the oral cavity and directed to the design, manufacture or installation of a dental prosthesis at a dental site within the oral cavity, or a real or virtual model thereof, or directed to the design and preparation of the dental site to receive such a prosthesis. A prosthesis may include any restoration such as crowns, veneers, inlays, onlays, and bridges, for example, and any other artificial partial or complete denture. The term orthodontic procedure refers, inter alia, to any procedure involving the oral cavity and directed to the design, manufacture or installation of orthodontic elements at a dental site within the oral cavity, or a real or virtual model thereof, or directed to the design and preparation of the dental site to receive such orthodontic elements. These elements may be appliances including but not limited to brackets and wires, retainers, clear aligners, or functional appliances.

A user (e.g., a practitioner) may navigate through scanning segments via a user interface (UI) of the intraoral scan application 108 by various input devices, such as a cursor control device (e.g., a mouse) or a touch input device (e.g., touchscreen). To use such means in some systems, the user typically disengages from the patient to engage the computing device 105 to operate the intraoral scan application 108. For example, a treatment plan may indicate that an upper arch region, lower arch region, and bite region of a patient are to be scanned. Traditionally, the user navigates the user interface to prepare the intraoral scan application 108 for the scanning of the upper arch region using a touchscreen or mouse device. The user then moves back to the patient to perform a scan for the upper arch region. The user then moves to the computing device to navigate to the next segment to be scanned. The user once again moves back to the patient to perform the next segment scan. The user repeats the process until all segments are properly scanned.

In embodiments, a touch sensitive scanner 150 may allow the user to easily navigate or control the user interface of the intraoral scan application 108 using the touch input of the touch sensitive scanner 150, thereby minimizing instances of the user moving between the computing device and the patient. For example, the user may utilize a combination of buttons and various touch gestures on the touch sensor of the touch sensitive scanner 150 to navigate the intraoral scan application 108 without moving to the computing device 105 to navigate or control the user interface.

Intraoral scan application 108 may include various modules to facilitate intraoral scanning procedures. In one embodiment, intraoral scan application 108 includes a touch input module 122, a patient module 115, a scan module 118, an image processing module 125, and a delivery module 120. Intraoral scan application 108 may additionally include a user interface 112, such as a graphical user interface (GUI). In alternative embodiments, the functionality of one or more of the touch input module 122, patient module 115, scan module 118, image processing module 125, and/or delivery module 120 may be combined into a single module or divided into multiple additional modules.

User interface 112 may be a GUI that receives user commands and provides a graphical and/or audio output to a user. The user interface 112 enables users to interact with intraoral scan application 108 through manipulation of graphical elements such as graphical icons and visual indicators such as buttons, menus, and so on. Intraoral scan application 108 may include a number of modes, such as a planning mode, a scan mode, an image processing mode, and a delivery mode. The user interface 112 may display different graphical elements for each of the various modes.

Navigation or control of the user interface 122 of the intraoral scan application 108 may be performed via user input. The user input may be performed through various devices, such as a touch input device (e.g., a touchscreen), keyboard, mouse, or other similar control devices. Use of such devices may include the user sitting within arm's length reach of the computing device 105, which may be inconvenient when performing scanning. Alternatively, the user may also opt to physically move from the patient to the computing device 105 as necessary to navigate the user interface or scan the patient, which may also be cumbersome. Navigation of the user interface may involve, for example, navigating between various modules or modes, navigating between various segments, controlling the viewing of the 3D rendering, or any other user interface navigation. Such navigation can be an inefficient process due to the user continuously disengaging and reengaging the patient. A touch sensitive scanner 150 allows the user to navigate or control the user interface without continuously disengaging from the patient.

Touch input module 122 receives and interprets touch input data from touch sensitive scanner 150. Touch sensitive scanner 150 may receive different types of touch input such as hold gestures, swipe gestures, tap gestures, circular gestures, and so on. Touch input module 122 may determine a type of touch gesture that a user performed based on the received touch input. Touch input module 122 may then initiate functions or operations of the user interface (or intraoral scan application generally) responsive to the determined touch gesture. The functions or operations that are initiated may depend both on the current mode of the intraoral scan application 108 and the determined touch gesture. Accordingly, the same touch gesture may cause a first function to be performed in a first mode of the intraoral scan application and may cause a second function to be performed in a second mode. Specific modes of operation and touch gestures that initiate operations or functions for those modes are discussed in greater detail below.

Touch gestures may also be used to navigate between modes of operation. In one embodiment, the touch input module 122 enables a user to use the touch sensitive scanner 150 to navigate through multiple levels of controls using touch gestures. In one embodiment, a user uses up and down swipe gestures to navigate through the levels of controls. For example, a user may provide an upward swipe gesture to navigate upward one level and a downward swipe gesture to navigate down one level. Each level of controls may provide a specific type of functionality, which may also depend on a current mode of operation of the intraoral scan application 108. Alternatively, upward and downward swipe gestures may be used to navigate between modes of operation without the use of multiple levels of controls.

In one embodiment, an orientation of the touch sensitive scanner 150 relative to a display of the computing device 105 is user configurable. Alternatively, an orientation of the touch sensitive scanner 150 relative to the display may automatically be detected (e.g., by use of a camera or infrared sensor on the touch sensitive scanner 150 and/or display). The different orientations may be a first orientation with a probe of the touch sensitive scanner towards the display or a second orientation with the probe directed away from the display. Depending on the current orientation, one side of the touch sensor may be designated as the left side and the other side may be designated as the right side.

In one embodiment, the multiple levels include at least a mode selection level and a mode interaction level. While in the mode selection level, a user may provide left and right swipe gestures to navigate between modes. From any mode of operation a user may provide an upward swipe gesture to navigate from the mode interaction level for that mode to the mode selection level. The user may then provide one or more sideways swipes to navigate to a new mode, and then provide a downward swipe gesture to navigate to a mode interaction level for the current mode of operation. The available functions while in the mode interaction level may depend on the current mode of operation.

Patient module 115 provides a planning mode for intraoral scan application 108 that allows a user (e.g., dental practitioner) to generate a patient profile and/or treatment plan for a patient. The patient profile may include information such as patient name, patient contact information, patient dental history, and so on. The patient's information may be entered into the intraoral scan application 108 by means of a keyboard or a touchscreen with a virtual on-screen keyboard on the user interface. The treatment plan may include dental procedures to be performed and/or teeth to which the dental procedures are to be performed. Some treatment plans include an indication of specific patient teeth that are to be preparation teeth.

For many prosthodontic procedures (e.g., to create a crown, bridge, veneer, etc.), an existing tooth of a patient is ground down to a stump. The ground tooth is referred to herein as a preparation tooth, or simply a preparation. The preparation tooth has a finish line (also referred to as a margin line), which is a border between a natural (unground) portion of the preparation tooth and the prepared (ground) portion of the preparation tooth. The preparation tooth is typically created so that a crown or other prosthesis can be mounted or seated on the preparation tooth. In many instances, the finish line of the preparation tooth is below the gum line. While the term preparation typically refers to the stump of a preparation tooth, including the finish line and shoulder that remains of the tooth, the term preparation herein also includes artificial stumps, pivots, cores and posts, or other devices that may be implanted in the intraoral cavity so as to receive a crown or other prosthesis. Embodiments described herein with reference to a preparation tooth also apply to other types of preparations, such as the aforementioned artificial stumps, pivots, and so on.

Once a patient profile and/or treatment plan are generated, intraoral scan application 108 may enter a scan mode provided by scan module 118. A user may transition from the planning mode to the scan mode by providing touch input in the form of one or more swipe gestures. The scan module 118 provides the scan mode, which allows the user to capture images and/or video (e.g., for lower arch segment, upper arch segment, bite segment, and/or preparation tooth segments). The images and/or video may be used to generate a virtual 3D model of a dental site.

In one embodiment, the scan mode includes multiple scan segments, which may be dependent on the treatment plan. There may be a different scan segment for an upper arch (or portion thereof), a lower arch (or portion thereof), a bite, and/or one or more preparation teeth. In one embodiment, a different scan segment is created for each preparation tooth. While in the mode interaction level and/or scan mode, the user may provide touch gestures to navigate between scan segments that are to be scanned (e.g., by providing left and right swipe gestures).

In one embodiment, touch input module 122 disables the touch sensor of the touch sensitive scanner 150 while a scan is being performed. The touch sensor may be disabled to ensure that the user does not inadvertently perform a touch gesture during a scan. In one embodiment, the touch sensor is automatically disabled when the touch sensitive scanner 150 detects an object in a field of view of a scanner head of the touch sensitive scanner 150. The scan mode is described in further detail in FIG. 4 below.

Once scans for the various scan segments are complete, intraoral scan application 108 may enter an image processing mode provided by image processing module 125. A user may transition from the scan mode to the image processing mode by providing touch input in the form of one or more swipe gestures. The image processing module 125 may process the intraoral scan data from the one or more scans of the various segments to generate a virtual 3D model of a scanned dental site.

In one embodiment, image processing module 125 performs image registration for each pair of adjacent or overlapping intraoral images (e.g., each successive frame of an intraoral video). Image registration algorithms are carried out to register two adjacent intraoral images, which essentially involves determination of the transformations which align one image with the other, Image registration may involve identifying multiple points in each image (e.g., point clouds) of an image pair, surface fitting to the points of each image, and using local searches around points to match points of the two adjacent images. For example, image processing module 125 may match points of one image with the closest points interpolated on the surface of the other image, and iteratively minimize the distance between matched points. Image processing module 125 may also find the best match of curvature features at points of one image with curvature features at points interpolated on the surface of the other image, without iteration. Image processing module 125 may also find the best match of spin-image point features at points of one image with spin-image point features at points interpolated on the surface of the other image, without iteration. Other techniques that may be used for image registration include those based on determining point-to-point correspondences using other features and minimization of point-to-surface distances, for example. Other image registration techniques may also be used.

Many image registration algorithms perform the fitting of a surface to the points in adjacent images, which can be done in numerous ways. Parametric surfaces such as Bezier and B-Spline surfaces are most common, although others may be used. A single surface patch may be fit to all points of an image, or alternatively, separate surface patches may be fit to any number of a subset of points of the image. Separate surface patches may be fit to have common boundaries or they may be fit to overlap. Surfaces or surface patches may be fit to interpolate multiple points by using a control-point net having the same number of points as a grid of points being fit, or the surface may approximate the points by using a control-point net which has fewer number of control points than the grid of points being fit. Various matching techniques may also be employed by the image registration algorithms.

In one embodiment, image processing module 125 may determine a point match between images, which may take the form of a two dimensional (2D) curvature array. A local search for a matching point feature in a corresponding surface patch of an adjacent image is carried out by computing features at points sampled in a region surrounding the parametrically similar point. Once corresponding point sets are determined between surface patches of the two images, determination of the transformation between the two sets of corresponding points in two coordinate frames can be solved. Essentially, an image registration algorithm may compute a transformation between two adjacent images that will minimize the distances between points on one surface, and the closest points to them found in the interpolated region on the other image surface used as a reference.

Image processing module 125 may repeat image registration for all adjacent image pairs of a sequence of intraoral images to obtain a transformation between each pair of images, to register each image with the previous one. Image processing module 125 then integrates all images into a single virtual 3D model by applying the appropriate determined transformations to each of the images. Each transformation may include rotations about one to three axes and translations within one to three planes.

While in the image processing mode, a user may view the 3D model in detail to determine if it is acceptable. The image processing mode allows the dental practitioner to view the scans in detail at various angles by rotating, moving, zooming in or out, etc. of the 3D model. The dental practitioner may make a determination whether the quality of the scans are adequate, or whether particular segments or portions of segments should be rescanned. The dental practitioner may also navigate back to the scan mode to perform additional scans.

In one embodiment, the user may provide a hold gesture via the touch sensor. Responsive to the hold gesture, touch input module 122 may activate a gyroscope and/or an accelerometer of the touch sensitive scanner 150, While the gyroscope and/or accelerometer are active, touch input module 122 may receive rotation and/or acceleration information based on a user moving the touch sensitive scanner 150. For example, the user may reposition the touch sensitive scanner from a first orientation to a second orientation, Based on the rotation and/or acceleration information, intraoral scan application 108 may change a view of the virtual 3D model from a first view having a first orientation of the 3D model to a second view having a second orientation of the 3D model. The change from the first view to the second view may correspond to the change from the first orientation to the second orientation of the touch sensitive scanner 150. In embodiments, a 3D rendering such as a preliminary or partial virtual 3D model may be created and updated as scan data is obtained. The above described hold gesture may also be performed during the scan mode to change a view of the 3D rendering (e.g., the preliminary or partial virtual 3D model).

Once the scans are complete, the delivery module 120 provides a delivery mode that allows the user to send the scans and/or virtual 3D model out to an external facility to process the scans or 3D model. A user may transition from the scan mode to the image processing mode by providing touch input in the form of one or more swipe gestures.

The following non-limiting example may help understand the process more fully. A patient who wishes to straighten their teeth may opt for Invisalign® treatment. Invisalign is a process that creates a custom made series of clear aligners specifically for the patient. The clear aligners are worn over the patient's teeth and gradually shift the patient's teeth. A new set of aligners may be worn after a specified period of time (e.g., two weeks) until treatment is complete. The patient may visit a dental practitioner or orthodontist to begin Invisalign treatment. The dental practitioner may utilize a scanning system, such as the iTero scanning system, to scan the patient's teeth and generate 3D models used to create the clear aligners. The scanning system may be a system 100 which includes touch sensitive scanner 150 coupled to a computing device 105 executing intraoral scan application 108. The dental practitioner would begin the Invisalign treatment by entering the patient's information into a patient profile and/or creating a treatment plan in the planning mode. The Invisalign treatment may call for a scan of the patient's lower arch, upper arch, and bite segments. Once the dental practitioner completes the patient profile and/or treatment plan, the dental practitioner may navigate to the scan mode to begin scanning. The scan mode may present a user interface to the dental practitioner similar to user interface 400 of FIG. 4 to be discussed in further detail below.

Figure 2:
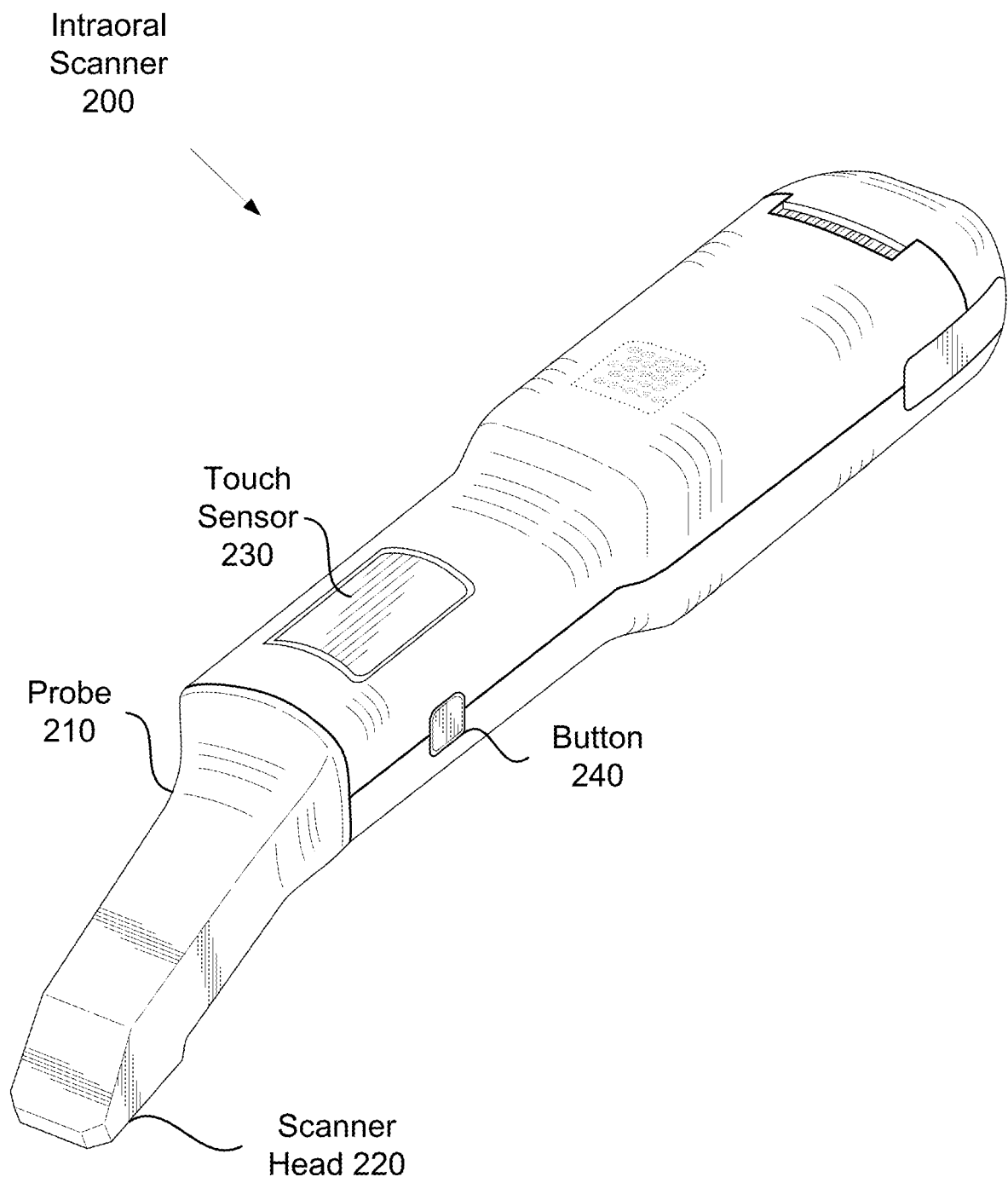
FIG. 2 illustrates a perspective view of an intraoral scanner with touch sensitive input.

The dental practitioner may use touch sensitive scanner 150 (e.g., intraoral scanner) to capture the patient's teeth segments (e.g., upper arch, lower arch, bite segments) in one or more sets of intraoral images. The scan module 118 may register and stitch together the intraoral images to create a 3D rendering of the scanned segments and present the 3D renderings to the dental practitioner on the user interface of the intraoral scan application 108. Once the scans are completed, the dental practitioner may next navigate to the image processing mode, which may generate a virtual 3D model by registering and stitching together the intraoral images. Once an adequate set of 3D renderings and/or virtual 3D model are complete, the 3D renderings may be saved to the patient profile. The dental practitioner may then navigate to the delivery mode to electronically send the completed patient profile to a processing center. The processing center may then generate the custom made series of clear aligners for the patient and deliver the clear aligners to the dental practitioner. The patient would then return to the dental practitioner to receive the first set of clear aligners and verify the clear aligners properly fit onto the patient's teeth, FIG. 2 illustrates a perspective view of an intraoral scanner 200 with touch sensitive input. The intraoral scanner 200 may alternatively be a medical scanning device for scanning objects other than an intraoral cavity. Other types of medical scanning devices 200 to which embodiments of the present invention may apply include other types of optical scanners, x-ray devices, ultrasound devices, and so on. Each such medical scanning device may include at the least an image sensor to generate medical images, a communication module to transmit the medical images to a computing device, and a touch sensor usable to manipulate the medical images on the computing device and/or a representation of a scanned object generated from the medical images. These components may be coupled together directly or via a bus. The touch sensor may also be usable to navigate a user interface of a medical scan application running on the computing device. The medical scanning devices may additionally include one or more buttons that may be used both to initiate generation of the medical images and to activate and/or deactivate the touch sensor.

In one embodiment, intraoral scanner 200 corresponds to touch sensitive scanner 150 of FIG. 1. The intraoral scanner 200 may include a probe 210 that protrudes from one end of a body of the intraoral scanner 200. The probe 210 may include a scanner head 220 that captures optical data and provides the optical data to one or more optical sensors disposed within the intraoral scanner 200.

In one embodiment, intraoral scanner 200 includes a semiconductor laser unit that emits a focused light beam. The light beam may pass through an illumination module disposed within the intraoral scanner 200, which splits the light beam into an array of incident light beams. The illumination module may be, for example, a grating or a micro lens array that splits the light beam into an array of light beams. In one embodiment, the array of light beams is an array of telecentric light beams. Alternatively, the array of light beams may not be telecentric.

Intraoral scanner 200 may further include a unidirectional mirror or beam sputter (e.g., a polarizing beam sputter) that passes the array of light beams. A unidirectional mirror allows transfer of light from the semiconductor laser through to downstream optics, but reflects light travelling in the opposite direction. A polarizing beam splitter allows transfer of light beams having a particular polarization and reflects light beams having a different (e.g., opposite) polarization. In one embodiment, as a result of a structure of the unidirectional mirror or beam sputter, the array of light beams will yield a light annulus on an illuminated area of an imaged object within a field of view of the scanner head 220 as long as the area is not in focus. Moreover, the annulus will become a completely illuminated spot once in focus. This ensures that a difference between measured intensities of out-of focus points and in-focus points will be larger.

Along an optical path of the array of light beams after the unidirectional mirror or beam splitter, intraoral scanner 200 may include confocal focusing optics, and probe 210 (also referred to as an endoscopic probing member). Additionally, a quarter wave plate may be disposed along the optical path after the unidirectional mirror or beam splitter to introduce a certain polarization to the array of light beams. In some embodiments this may ensure that reflected light beams will not be passed through the unidirectional mirror or beam sputter.

The probe 210 may internally include a rigid, light-transmitting medium, which may be a hollow object defining within it a light transmission path or an object made of a light transmitting material, e.g. a glass body or tube. In one embodiment, the probe 210 includes a prism such as a folding prism. At the end of the probe 210 where the scanner head 220 is located, the probe 210 may include a mirror of the kind ensuring a total internal reflection. Thus, the mirror may direct the array of light beams towards a teeth segment or other object. The scanner head 220 thus emits array of light beams, which impinge on to surfaces of scanned objects such as teeth.

The array of light beams may be are arranged in an X-Y plane. As the surface on which the incident light beams hits is an uneven surface, illuminated spots are displaced from one another along the Z axis, at different ($X_i$, $Y_i$) locations. Thus, while a spot at one location may be in focus of the confocal focusing optics, spots at other locations may be out-of-focus. Therefore, the light intensity of returned light beams of the focused spots will be at its peak, while the light intensity at other spots will be off peak. Thus, for each illuminated spot, multiple measurements of light intensity are made at different positions along the Z-axis. For each of such ($X_i$, $Y_i$) location, the derivative of the intensity over distance (Z) may be made, with the $Z_i$ yielding maximum derivative, $Z_0$, being the in-focus distance. As pointed out above, the incident light from the array of light beams forms a light disk on the surface when out of focus and a complete light spot when in focus. Thus, the distance derivative will be larger when approaching in-focus position, increasing accuracy of the measurement.

The light scattered from each of the light spots includes a beam travelling initially in the Z axis along the opposite direction of the optical path traveled by the array of light beams. Each returned light beam in an array of returning light beams corresponds to one of the incident light beams in array of light beams. Given the asymmetrical properties of unidirectional mirror or beam splitter, the returned light beams are reflected in the direction of detection optics (e.g., one or more optical sensors).

The optical sensor may be an image sensor having a matrix of sensing elements each representing a pixel of the image. In one embodiment, the optical sensor is a charge coupled device (CCD) sensor. In one embodiment, the optical sensor is a complementary metal-oxide semiconductor (CMOS) type image sensor. Other types of image sensors may also be used. The optical sensor detects light intensity at each pixel.

Intraoral scanner 200 may further include a control module connected both to the semiconductor laser and a motor, voice coil or other translation mechanism. The motor may be linked to confocal focusing optics for changing a focusing setting of confocal focusing optics. After receipt of feedback that the location of the one or more lenses has changed, the control module may induce the laser to generate a light pulse. The control unit may additionally synchronize the image-capturing module to receive and/or store data representative of the light intensity from each of the sensing elements at the particular location of the one or more lenses (and thus of the focal depth). In subsequent sequences, the location of the one or more lenses (and thus the focal depth) will change in the same manner and the data capturing will continue over a wide focal range of confocal focusing optics.

One embodiment of an intraoral scanner 200 that uses confocal imaging to generate 3D images has been described above. However, embodiments should be understood as covering all types of 3D imaging devices. For example, intraoral scanner 200 may include stereoscopic camera pairs for generating stereoscopic images, may use projections of structured light patterns to determine 3D information, and so on.

As illustrated, intraoral scanner 200 additionally includes multiple input devices. These input devices may include one or more buttons 240 and a touch sensor 230. In one embodiment, intraoral scanner 200 includes a pair of buttons disposed at opposite sides of the intraoral scanner 200. One of the buttons is hidden in the view of intraoral scanner 200 shown in FIG. 2. In one embodiment, each button 240 of the pair of buttons generates the same signals, and thus causes the same operations or functions to be performed. Depending on how a user holds intraoral scanner 200, one of the buttons may be more convenient to press than the other button. In one embodiment, simultaneously pressing the pair of buttons activates touch sensor 230. Alternatively, other button push combinations of one or both of the buttons may activate the touch sensor 230.

Touch sensor 230 is capable of detecting a user touch, and can receive multiple different types of touch gestures, such as swipes, holds, taps, and so on. A hold gesture may be detected when a user presses the touch sensor 230 for a threshold amount of time (e.g., a press duration of 1 second, 2 seconds, etc.). A swipe gesture may be detected when a user initially presses one side of the touch sensor 230 with a finger, and then moves their finger across to another side of the touch sensor 230. Touch sensor 230 may be a touchpad, trackpad or touch screen that can translate the motion and position of a user's fingers into touch gestures. Touch sensor 230 may include capacitive sensing elements, conductance sensing elements, infrared sensing elements, inductive sensing elements, and/or other sensing elements. Touch sensor 230 may be a one dimensional touchpad or a two dimensional touchpad.

The touch sensor 230 may detect a touch input gesture including, but not limited to, swipe gestures, hold gesture, single-finger touch gestures, and/or multi-finger touch gestures. Responsive to detecting a touch input, touch sensor 230 may generate touch input data (also referred to as a touch input signal) for a particular touch gesture and transmit the touch input data to a connected computing device. The touch input gesture may be used to control the user interface of the intraoral scan application 108. For example in scan mode, a swipe left and swipe right gesture may allow the user to navigate between teeth segments (e.g., lower arch segment, upper arch segment, and bite segment). A swipe up and swipe down gesture may allow the user to navigate between the various modules of the intraoral scan application 108 (e.g., patient module, scan module, image processing module, delivery module). The touch input gesture may also be used to manipulate medical data that has been generated by the intraoral scanner 200 and sent to a computing device. For example, a hold gesture may allow the user to activate an inertial measurement device and rotate a 3D rendering generated from medical images by rotating the intraoral scanner 200. The touch sensor 230 and at least one button 240 may be used in conjunction to perform additional control of the user interface, medical images, and/or representations generated from the medical images. For example, upon holding the button 240 in conjunction with a swipe up gesture, swipe down gesture or side swipe gesture on the touch sensor 230, the intraoral scan application 108 may launch an overlay mode similar to that shown in FIG. 7. In another example, holding the button 240 in conjunction with a swipe up gesture, swipe down gesture or side swipe gesture may cause the 3D rendering to zoom in or out.

In one embodiment, intraoral scanner 200 disables touch sensor 230 during scanning to ensure that a user will not inadvertently issue commands via the touch sensor 230. Accordingly, intraoral scanner 200 may automatically disable touch sensor 230 when an object is detected in a field of view of sensor head 220 and/or within a threshold distance from sensor head 230. Intraoral scanner 200 may additionally include one or more lights (e.g., light emitting diodes (LEDs)), which may be mounted to probe 210. These lights may be automatically activated when an object is detected in the field of view of the sensor head 220.

In one embodiment, intraoral scanner 200 includes an inertial measurement device. The inertial measurement device may include one or more accelerometers and/or one or more gyroscopes, that may help determine the intraoral scanner's 200 velocity, orientation, rotation, movement, and/or gravitational forces. Additionally, an inertial measurement device may include a magnetic sensor. A magnetic sensor may allow the inertial measurement device to determine the rotation position of the intraoral scanner 200. Raw inertial measurement data may be processed to help determine the orientation of intraoral scanner 200. Raw inertial measurement data and processed inertial measurement data may be referred to as inertial measurement data.

In one embodiment, intraoral scanner 200 activates the inertial measurement device (or devices) responsive to touch sensor 230 detecting a hold gesture. In one embodiment, while the user continues the hold gesture, inertial measurement data generated by the inertial measurement device is used to control the view and orientation of a virtual 3D model. Alternatively, once the hold gesture is received, the inertial measurement data may continue to be used for controlling the view and orientation of the virtual 3D model.

Figure 3A:
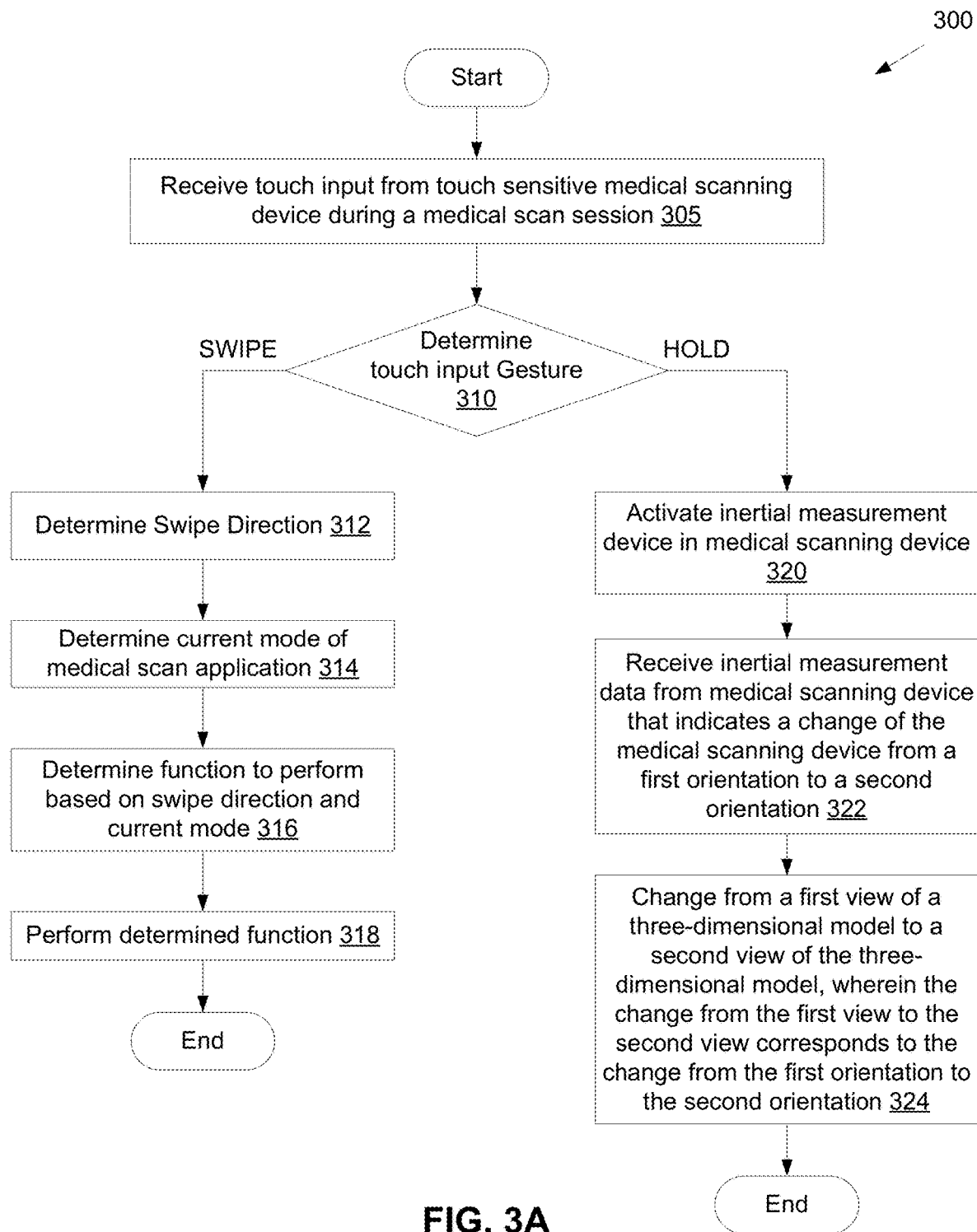
FIG. 3A illustrates a flow diagram for a method of receiving a touch input from a touch sensitive intraoral scanner and performing a determined function during an intraoral scan session, in accordance with embodiments of the present invention.

FIG. 3A illustrates a flow diagram for a method 300 of receiving a touch input from a touch sensitive intraoral scanner and performing a determined function to control a user interface of an intraoral scan application during an intraoral scan session, in accordance with embodiments of the present invention. This method may be performed by processing logic that comprises hardware (e.g., circuitry, dedicated logic, programmable logic, microcode, etc.), software (such as instructions run on a processing device), or a combination thereof. In one embodiment, processing logic corresponds to computing device 105 of FIG. 1 (e.g., to a computing device 105 executing intraoral scan application 108).

By way of non-limited example, method 300 may occur during an oral scan session of a patient by a dental practitioner. At block 305, processing logic receives a touch input from a touch sensitive intraoral scanner during a medical scan session 305. The touch input may include a swipe gesture, a hold gesture, a tap gesture, or some other gesture. At block 310, processing logic determines whether the touch input gesture is one of a swipe gesture or a hold gesture.

At block 312, upon determining the touch input gesture is a swipe gesture, processing logic determines a swipe direction of the swipe gesture. The swipe direction may include, but is not limited to, a swipe left gesture, a swipe right gesture, a swipe up gesture, and a swipe down gesture. The swipe direction may also be a diagonal swipe direction.

At block 314, processing logic determines a current mode of the intraoral scan application. For example, the current mode may be a planning mode, a scanning mode, an image processing mode or a delivery mode. Determining the current mode of the intraoral scan application may include determining an active module and a current focus of the active module. In one embodiment, the active module may be patient module, scan module, image processing module, or delivery module. The current focus of the active module describes an active or highlighted section of the active module. For example, a dental practitioner preparing to scan the lower arch segment of a patient may navigate to the lower arch segment of a scan mode presented by the scan module. In such a case, the lower arch segment may be the current focus of the active module, and the scan module may be the active module. For example, FIG. 4, which will be described in further detail below, provides an illustration of the current focus of the active module (e.g., lower arch segment) and the active module (e.g., scan mode) denoted by highlights around the aforementioned sections.

At block 316, processing logic determines a function to perform based on swipe direction and current mode. The function to perform may include an action or operation which may cause the current focus of the active module to move to a next focus. For example, if the current focus is the upper arch segment of the scan mode, processing logic may determine that a swipe right gesture will change the current focus to the next segment (e.g., bite segment) in scan mode, or a swipe left gesture may change the current focus to the previous segment (e.g., lower arch segment) in scan mode. At block 318, processing logic performs the determined function (e.g., switches to the next or previous focus).

The function that is determined at block 316 may also depend on a current active level. In one embodiment, processing logic provides multiple levels that may include, for example, a mode selection level and a mode interaction level. While in the mode selection level, a user may provide left and right swipe gestures to navigate between modes. While in a mode interaction level, a user may provide left and right swipe gestures to switch a focus to a next or previous segment, for example.

At block 320, upon determining the touch input gesture is a hold gesture, processing logic activates an inertial measurement device in the intraoral scanner. Once activated, the inertial measurement device may generate inertial measurement data (e.g., velocity, orientation, gravitational forces, and/or rotational position) of the intraoral scanner. At block 322, processing logic receives inertial measurement data from the intraoral scanner that indicates a change of the intraoral scanner from a first orientation to a second orientation. For example, processing logic may receive data from the intraoral scanner that the intraoral scanner was rotated 45 degrees in a downward direction. At block 324, processing logic may perform a view function to change from a first view of a 3D model to a second view of the 3D model, wherein the change from the first view to the second view corresponds to the change from the first orientation to the second orientation of the intraoral scanner. For example, upon receiving inertial measurement data that the intraoral scanner was rotated 45 degrees in a downward direction, processing logic may rotate the 3D rendering of an upper arch segment 45 degrees in a downward direction in correspondence with the inertial measurement data.

Figure 3B:
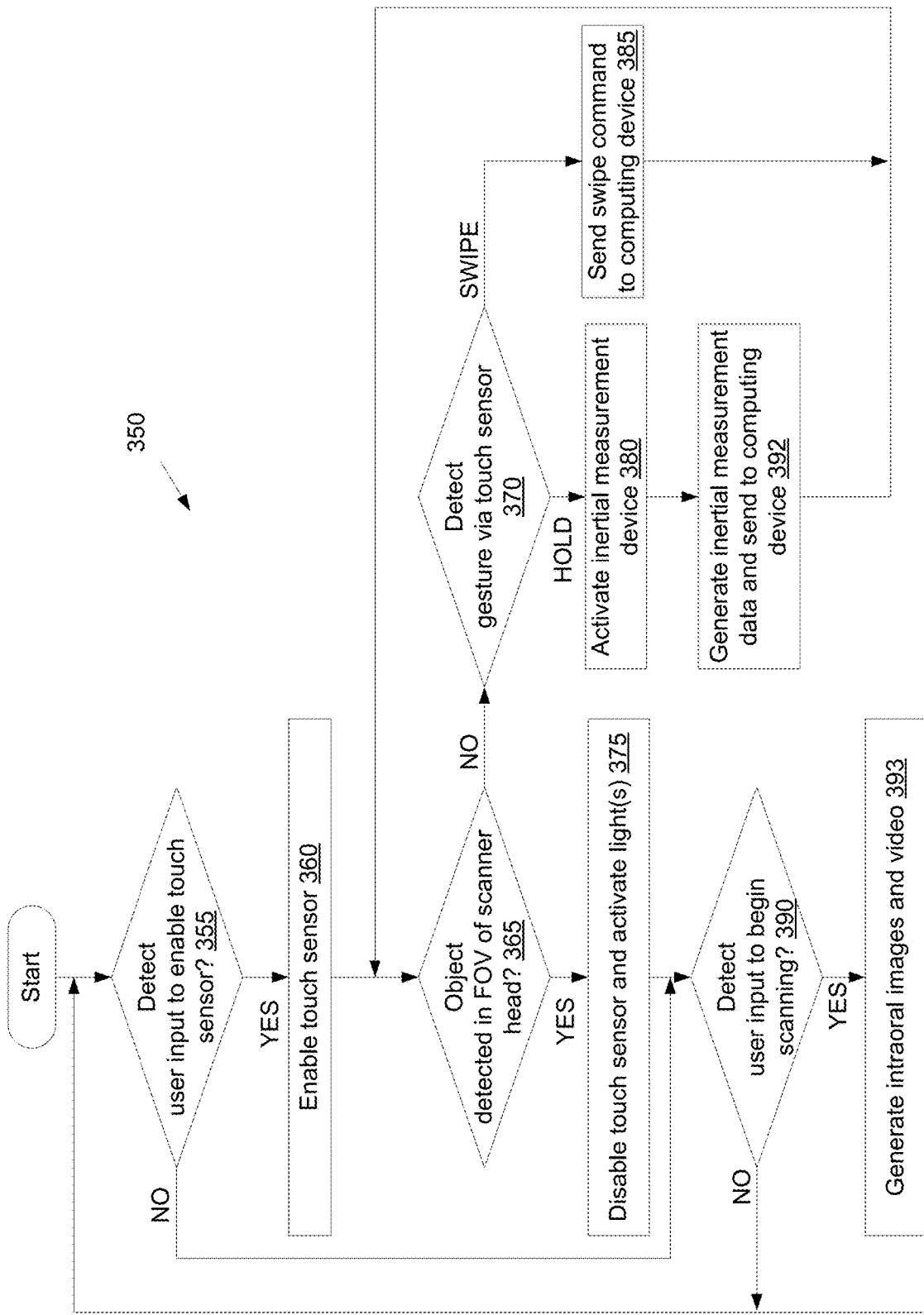
FIG. 3B illustrates a flow diagram for a method of enabling and disabling a touch sensor of an intraoral scanner and performing functions based on inputs from the touch sensor, in accordance with embodiments of the present invention.

FIG. 3B illustrates a flow diagram for a method 350 of enabling and disabling the touch sensor of a touch sensitive intraoral scanner and performing functions based on inputs from the touch sensor, in accordance with embodiments of the present invention. This method may be performed by processing logic that comprises hardware (e.g., circuitry, dedicated logic, programmable logic, microcode, etc.), software (such as instructions run on a processing device), or a combination thereof. In one embodiment, processing logic corresponds to intraoral scanner 200 of FIG. 2.

A touch sensor of the intraoral scanner may be disabled to prevent the user from performing unintended touch input. For example, a dental practitioner handling the intraoral scanner may accidentally brush a finger against the touch sensor during the course of a scan, which could cause the intraoral scan application to perform a determined function if the touch sensor is active.

At block 355, processing logic may detect user input to enable the touch sensor. In one embodiment, the intraoral scanner may include two buttons. For example, the user input to enable the touch sensor may come in the form of the simultaneous pressing of the two buttons. If no user input is detected to enable the touch sensor, processing logic moves to block 390. If the user input to enable the touch sensor is detected, the touch sensor is enabled at block 360.

At block 365, processing logic detects whether an object is in a field of vision (FOV) of scanner head of the intraoral scanner. For example, a patient's teeth may be detected when an intraoral scanner is inserted into the patient's mouth. In one embodiment, the scanner head's FOV is a variable distance. For example, the FOV may be configured as 13.5 millimeters×13.5 millimeters×13.5 millimeters (13.5 cubic millimeters), but may also be increased or decreased as needed. An ideal FOV for medical scans may be dependent on the type of scan. For intraoral scans, a FOV of less than 20 cubic millimeters may be appropriate. Processing logic may also determine at block 365 whether a detected object is within a threshold distance from the scanner head.

If no object is detected in the FOV of the scanner head, processing logic moves to block 370, where processing logic detects a gesture via the touch sensor. At block 385, if a swipe gesture (e.g., swipe left gesture, swipe right gesture, swipe up gesture, swipe down gesture) is detected, processing logic sends the swipe gesture to the computing device; processing logic then returns to block 365. If a hold gesture is detected, processing logic activates the inertial measurement device at block 380. At block 392, processing logic generates inertial measurement data and sends the data to the computing device; processing logic then returns to block 365.

Returning to block 365, if an object is detected in the FOV of the scanner head, processing logic moves to block 375 and disables the touch sensor and activates light(s) such as light emitting diodes (LEDs) that may be mounted to a probe of the intraoral scanner. For example, once the user inserts the intraoral scanner into the patient's mouth for scanning, the touch sensor may be disabled to prevent unintended touch input and lights near the scanner head may illuminate to provide lighting to the scanning area.

At block 390, processing logic detects user input to begin scanning. In some embodiments, the user input may be a press of a button of the intraoral scanner. If no user input to begin scanning is detected, processing logic returns to block 355. At block 393, upon detection of user input to begin scanning, processing logic generates intraoral images and/or video. For example, a dental practitioner may press a button of the intraoral scanner to begin an intraoral scan of a bite segment, for which intraoral images and/or video may be generated. The method may then return to block 355. Method 350 may continue until a user turns off the intraoral scanner.

Figure 3C:
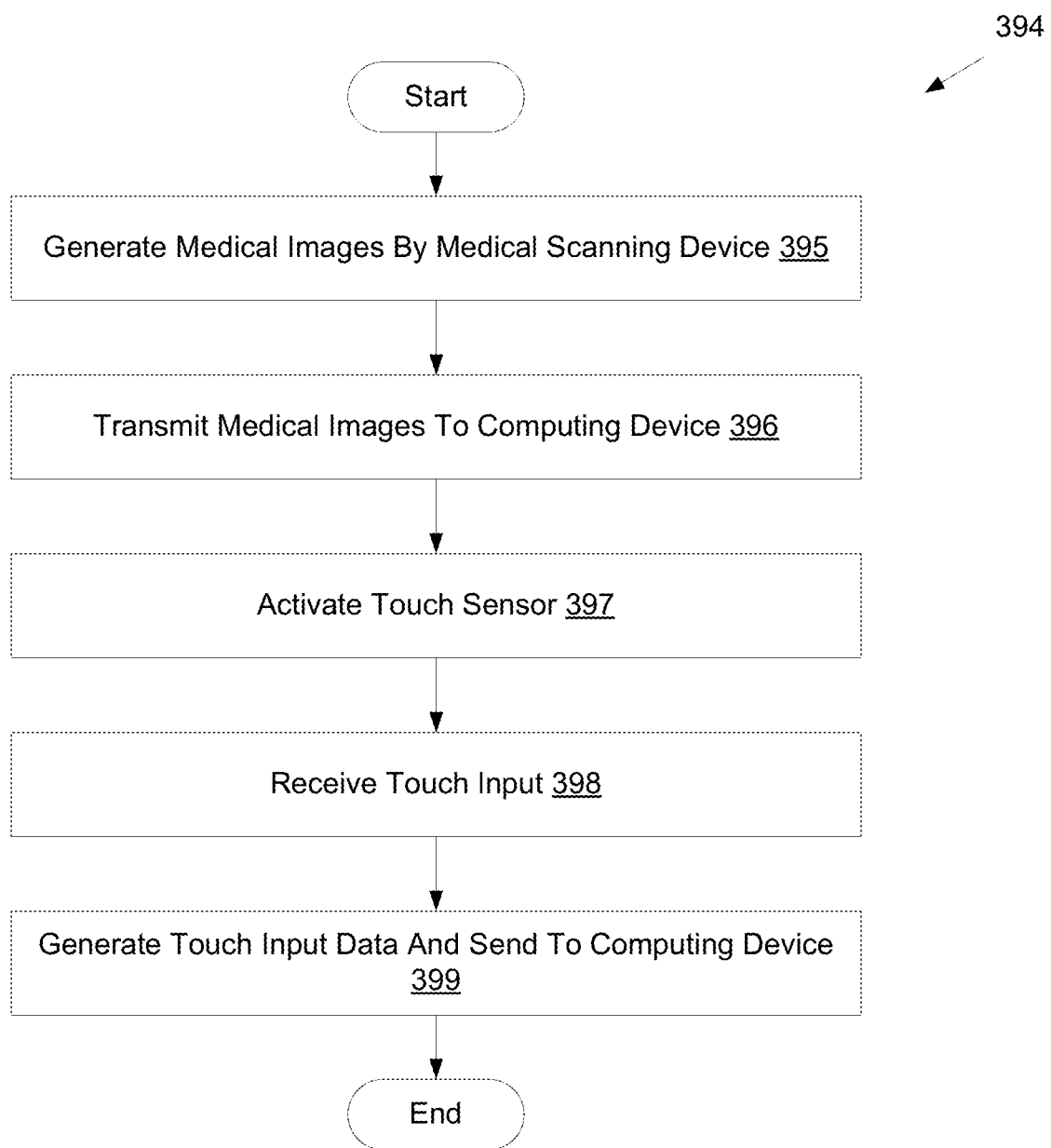
FIG. 3C illustrates a flow diagram for a method of generating medical images, providing the medical images to a computing device, and then manipulating those medical images on the computing device, in accordance with embodiments of the present invention.

FIG. 3C illustrates a flow diagram for a method 394 of generating medical images, providing the medical images to a computing device, and then manipulating those medical images on the computing device, in accordance with embodiments of the present invention. This method may be performed by a medical scanning device. In one embodiment, the medical scanning device corresponds to intraoral scanner 200 of FIG. 2. Alternatively, the medical scanning device may be another type of medical imaging device.

At block 395 of method 394, an image sensor of the medical scanning device generates one or more medical images. The image sensor may be an x-ray device, an ultrasound transceiver, an optical image sensor (e.g., CCD sensor, a CMOS type image sensor, etc.), or other type of image sensor.

At block 396, a communication module of the medical scanning device transmits the medical images to a computing device that is connected to the medical scanning device via a wired or wireless connection. The communication module may be a wireless communication module (e.g., a Wi-Fi network adapter, a Bluetooth transceiver, a Zigbee transceiver, an infrared transceiver, an ultrasound transceiver, etc.) or a wired communication module (e.g., an Ethernet network adapter, a USB module, etc.).

At block 397, the medical scanning device activates a touch sensor of the medical scanning device. The touch sensor may have been disabled while the medical images were being generated so as not to interfere with the image generation process (e.g., from an unintentional touch gesture). The touch sensor may be activated responsive to a user pressing one or more buttons of the medical scanning device. In one embodiment, a particular button push combination of a pair of buttons activates the touch sensor. For example, a simultaneous button push of the pair of buttons may activate the touch sensor.

At block 398, the medical scanning device receives a touch input (e.g., detects a user finger on the touch sensor). At block 399, the touch sensor may determine a touch gesture represented by the touch input, and may generate a corresponding touch input data or signal. The medical scanning device may then send the touch input data to the connected computing device. The touch input data may cause a medical scan application running on the computing device to perform one or more functions that may manipulate the medical images, manipulate a representation (e.g., virtual 3D model) generated from the medical images, navigate a UI of the medical scan application, and so on.

Figure 4:
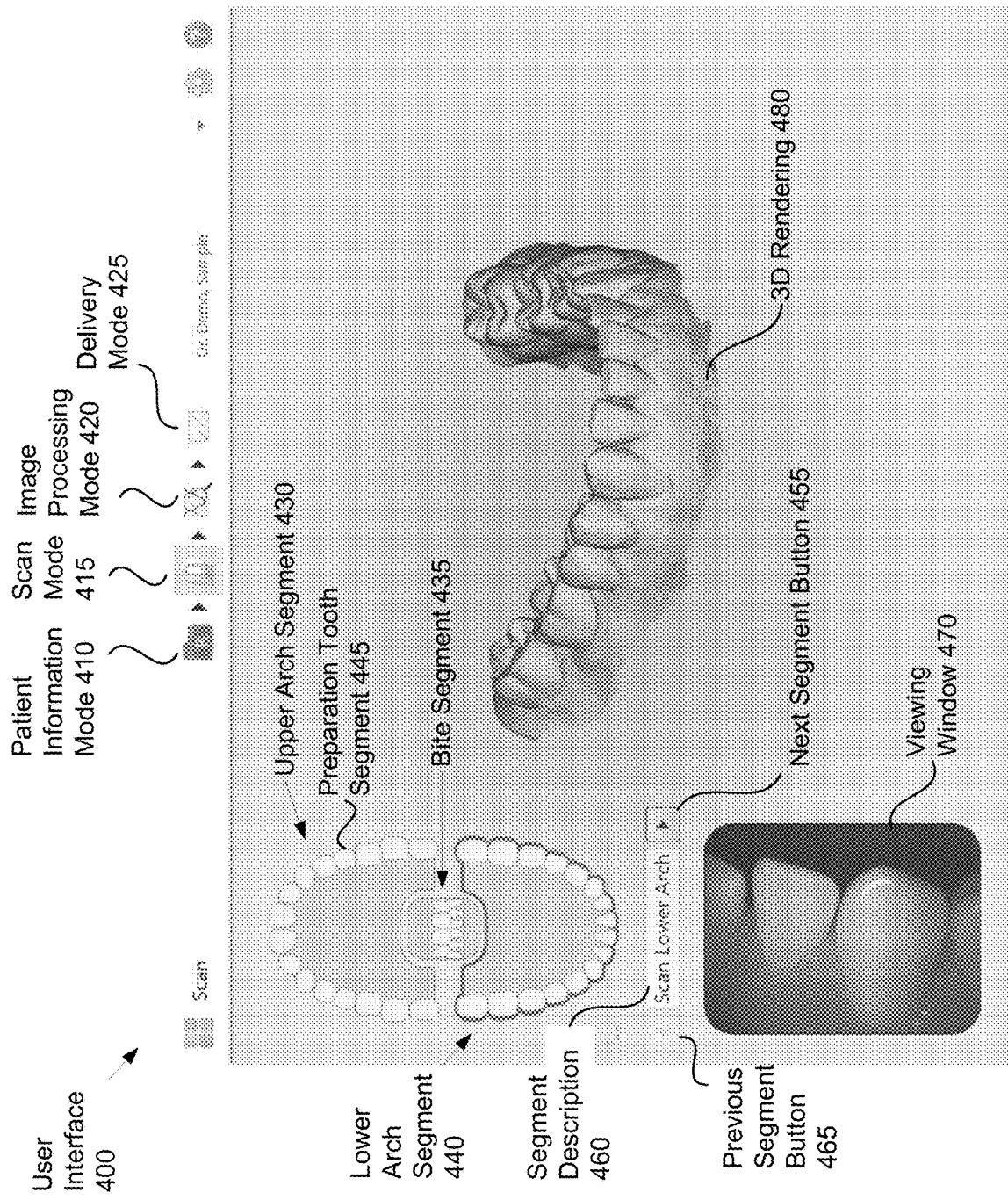
FIG. 4 illustrates an example scan mode user interface of an intraoral scan application.

FIG. 4 illustrates an example scan mode user interface (UI) 400 of an intraoral scan application (e.g., of intraoral scan application 108 of FIG. 1). The UI 400 may be interactive, and user interactive options may be represented as icons. The user may interact with the UI 400 by various input (e.g., mouse, keyboard, touchscreen, touch sensors from an intraoral scanner, or other similar devices).

At the top of the UI 400, icons for the patient information mode 410, scan mode 415, image processing mode 420, and delivery mode 425 are displayed. The active mode (e.g., scan mode 415 in this instance) is highlighted. The user may switch to a different mode by clicking the desired icon (e.g., with a mouse) or touching the icon (e.g., with a touchscreen). The user may alternatively utilize the touch input of the intraoral scanner to switch to a different mode. For example, a swipe up gesture may change from a mode interaction level to a mode selection level. Once in the mode selection level, a left or right swipe gesture may navigate between modes.

Various teeth segments are displayed on the upper left section of the UI 400. The upper arch segment 430, bite segment 435, lower arch segment 440, and an individual preparation tooth segment 445 are represented by icons. Depending on a treatment plan for a current patient, there may be no preparation tooth segments, one preparation tooth segment, or multiple preparation tooth segments. The preparation tooth segment 445 may be represented by any individual tooth corresponding to a patient's tooth that will be used as a preparation tooth. Alternatively, an upward swipe gesture may transition the intraoral scan application to a next mode.

Figure 6:
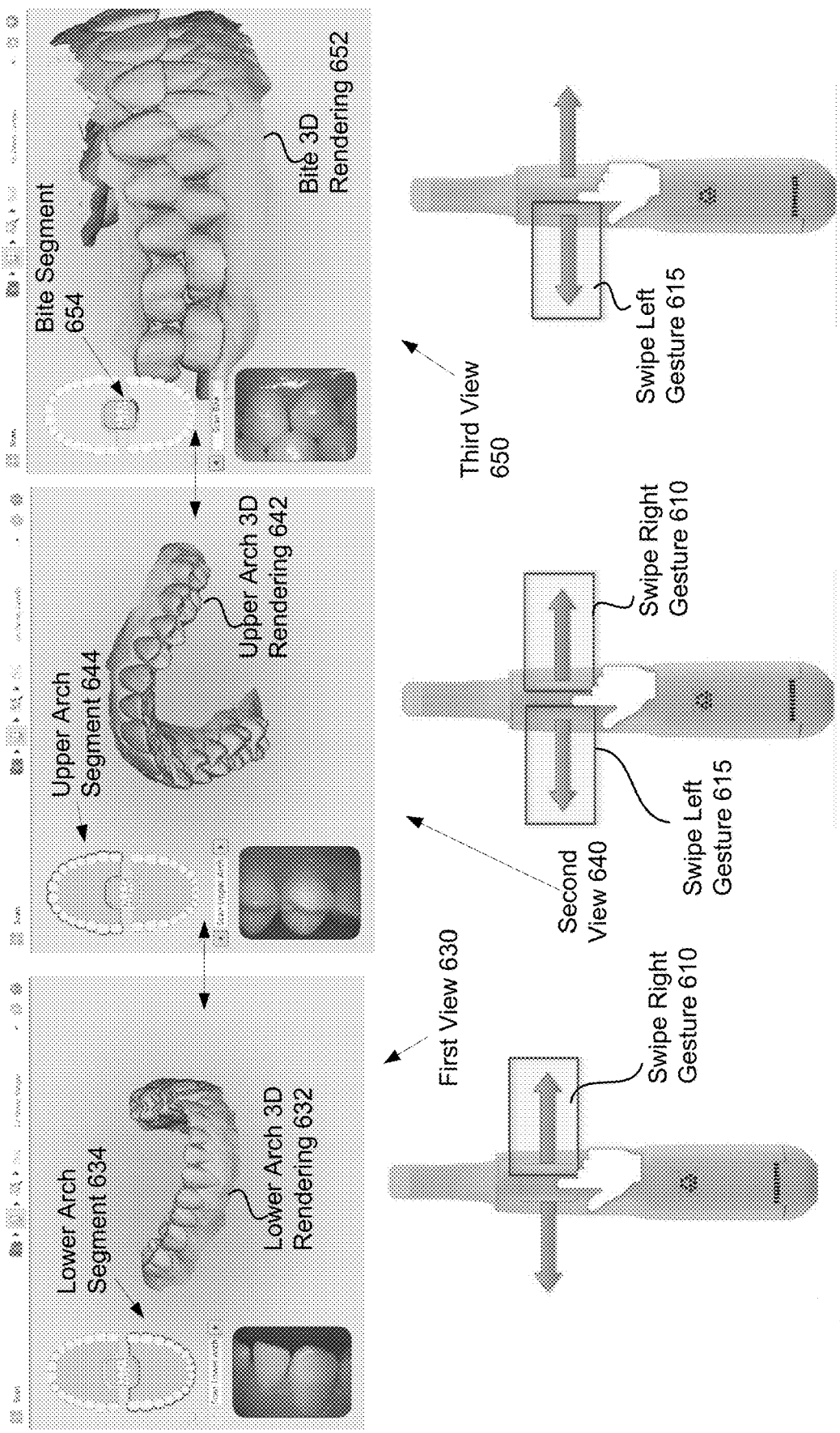
FIG. 6 illustrates example swipe gestures and resulting functions performed by an intraoral scan application.

While an intraoral scan application is in the mode interaction level for a scan mode, a user may generate intraoral data sets for each of the segments 430, 435, 440, 445. A user may select which of the segments to generate an intraoral data set for using any number of input devices. One such input device is the touch sensor integrated into the intraoral scanner. The segment that is the current focus is highlighted with an outline (e.g., lower arch segment 440). A segment description 460 provides a textual description of the segment that has the current focus (e.g., scan lower arch). The previous segment button 465 and next segment button 455 are user interactive, and allow the user to move the current focus to another tooth segment. A user may navigate between segments by using a touch screen or mouse to press the next segment button 455 or the previous segment button 465. Alternatively, the user may use the touch sensor of the intraoral scanner to input a swipe gesture. The focus may then switch to the next or previous segment based on the swipe gesture. For example, where the current focus is the upper arch segment 430, a swipe right gesture will change the current focus to the bite segment 435, or a swipe left gesture will change the current focus to the lower arch segment 440. FIG. 6 provides a further illustration of utilizing swipe gestures to change the current focus.

A viewing window 470 provides a live view of the objects in the field of view of the intraoral scanner. The viewing window 470 may provide an indication of images and/or video to be captured.

A 3D rendering 480 provides a rough virtual 3D model generated by stitching together images from an image data set generated for the segment that has the current focus (e.g., lower arch segment 440). A user may view the 3D model from various angles, and may zoom in or out. The user may use a touchscreen on the computing device 105 to move, rotate, and zoom in/out of the 3D model. The user may also utilize the touch sensor of the intraoral scanner to move, rotate and zoom in/out of the 3D model by activating and using data collected by the inertial measurement device as described in blocks 320-324 of FIG. 3A, and further described in FIG. 5.

Figure 5:
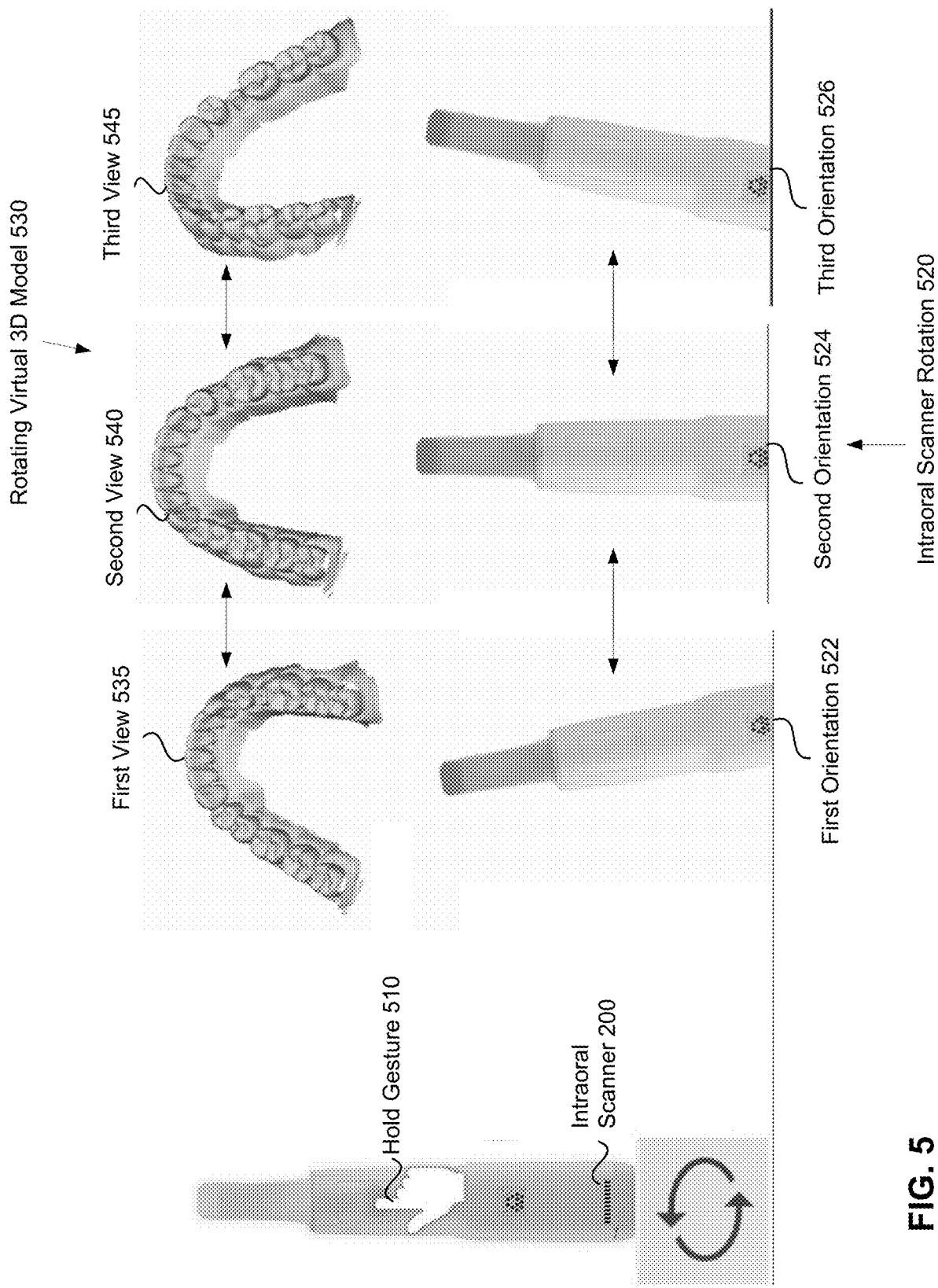
FIG. 5 illustrates an example rotation of an intraoral scanner and the resulting rotation of a virtual 3D model.

FIG. 5 illustrates a view function that triggers an example rotation of an intraoral scanner 520 and the resulting rotation of a virtual 3D model 530 generated based on an intraoral scan. A hold gesture 510 may be detected by a touch sensor of an intraoral scanner 200, which may activate an inertial measurement device of the intraoral scanner 200. Once the inertial measurement device is activated, inertial measurement data (e.g., rotational and/or acceleration data) may be generated as a user moves (e.g., rotates) the intraoral scanner 200. This inertial measurement data may be used to rotate and/or move the virtual 3D model. The virtual 3D model may then move concurrently with the intraoral scanner. For example, as the intraoral scanner 200 moves from a first orientation 522 to a second orientation 524 and on to a third orientation 526, the 3D model will move from a first view 535 corresponding to the first orientation 522 to a second view 540 corresponding to the second orientation 524, and on to a third view 545 corresponding to the third orientation 526. The intraoral scanner 200 may be rotated, moved in various directions, etc., and the 3D model will also move, rotate, etc. accordingly. Therefore, the dental practitioner may conveniently control the 3D model while still holding the intraoral scanner 200 without having to physically move within proximity of a computing device to utilize a mouse or touchscreen.

FIG. 6 illustrates example swipe gestures and resulting functions performed by an intraoral scan application in a scan mode of operation. A focus of the scan mode may initially be a lower arch segment 634, as shown in first view 630. The lower arch segment 634 is highlighted and a lower arch 3D rendering 632 is displayed in the first view 630.

The user may perform a swipe right gesture 610 on the intraoral scanner 200, which causes the Intraoral scan application 108 to move the current focus to the upper arch segment 644, as shown in second view 640. In the second view 640, the upper arch segment 644 is highlighted and the upper arch 3D rendering 642 is displayed.

The user may perform a swipe left gesture 615 to return the focus to the lower arch segment 630. Alternatively, the user may perform a swipe right gesture 610 to move the focus to the bite segment 650, as shown in third view 650. In the third view 650, the bite segment 654 is highlighted and a bite 3D rendering 652 is displayed.

Figure 7:
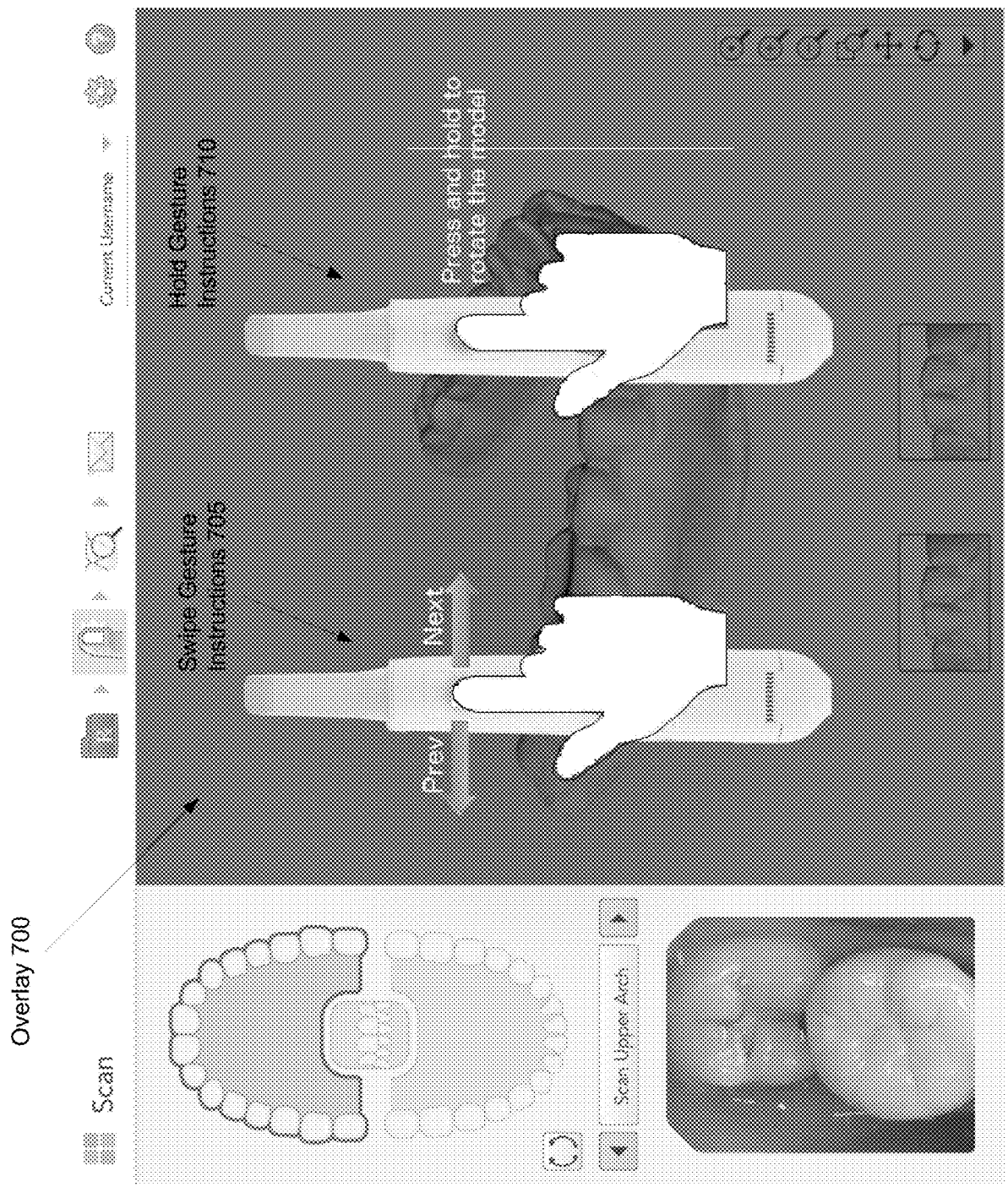
FIG. 7 illustrates an example overlay screen of a intraoral scan application.

FIG. 7 illustrates an example overlay 700 for an intraoral scan application 108. The overlay 700 may appear over various active modes (e.g., scan mode) and may provide assistance information regarding touch gestures that may be used for the particular active mode. For example, in the illustration overlay 700 provides instructional information regarding the use of the intraoral scanner 200 and available control functionality. Swipe gesture instructions 705 may provide the user information on a command that will be entered responsive to a swipe left gesture (e.g., a "Prev" or previous command) and a swipe right gesture (e.g., a "Next" command). Hold gesture instructions 710 may provide the user information on a command that will be entered responsive to a hold gesture (e.g., "Press and hold to rotate the model"). Overlay 700 may also provide additional information to assist the user in the scanning process, such as guidance as to scanning technique, and/or may highlight scan assistance indications (e.g., ones corresponding to missing and/or flawed scan data).

Figure 8:
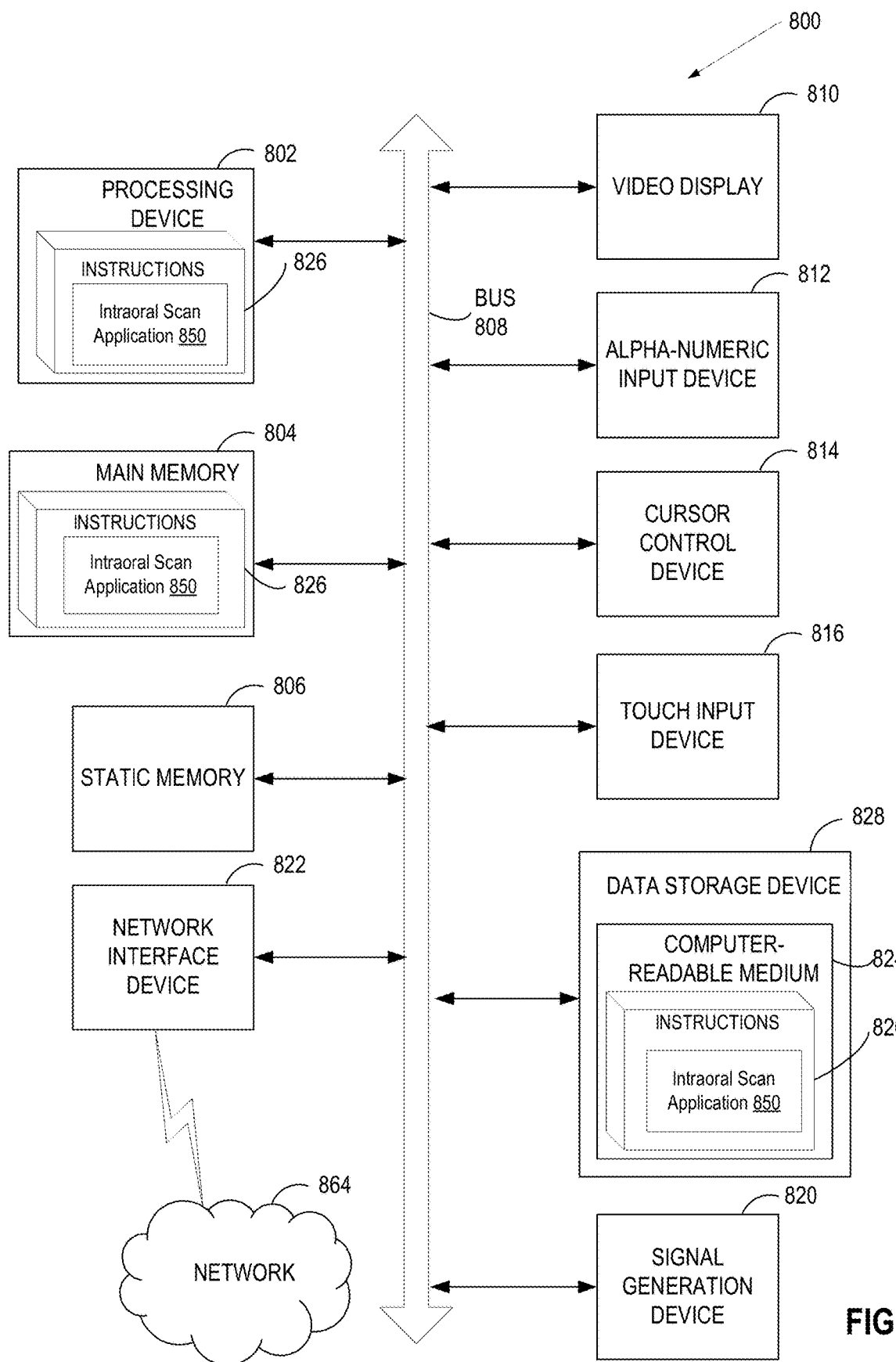
FIG. 8 illustrates a block diagram of an example computing device, in accordance with embodiments of the present invention.

FIG. 8 illustrates a diagrammatic representation of a machine in the example form of a computing device 800 within which a set of instructions, for causing the machine to perform any one or more of the methodologies discussed herein, may be executed. In alternative embodiments, the machine may be connected (e.g., networked) to other machines in a Local Area Network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein.

The example computing device 800 includes a processing device 802, a main memory 804 (e.g., read-only memory (ROM), flash memory, dynamic random access memory (DRAM) such as synchronous DRAM (SDRAM), etc.), a static memory 806 (e.g., flash memory, static random access memory (SRAM), etc.), and a secondary memory (e.g., a data storage device 828), which communicate with each other via a bus 808.

Processing device 802 represents one or more general-purpose processors such as a microprocessor, central processing unit, or the like. More particularly, the processing device 802 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 802 may also be one or more special-purpose processing devices such as an application specific integrated circuit (ASIC), a field programmable gate array (FPGA), a digital signal processor (DSP), network processor, or the like. Processing device 802 is configured to execute the processing logic (instructions 826) for performing operations and steps discussed herein.

The computing device 800 may further include a network interface device 822 for communicating with a network 864. The computing device 800 also may include a video display unit 810 (e.g., a liquid crystal display (LCD) or a cathode ray tube (CRT)), an alphanumeric input device 812 (e.g., a keyboard), a cursor control device 814 (e.g., a mouse), a touch input device 816 (e.g., a touchscreen), and a signal generation device 820 (e.g., a speaker).

The data storage device 828 may include a machine-readable storage medium (or more specifically a non-transitory computer-readable storage medium) 824 on which is stored one or more sets of instructions 826 embodying any one or more of the methodologies or functions described herein. A non-transitory storage medium refers to a storage medium other than a carrier wave. The instructions 826 may also reside, completely or at least partially, within the main memory 804 and/or within the processing device 802 during execution thereof by the computer device 800, the main memory 804 and the processing device 802 also constituting computer-readable storage media.

The computer-readable storage medium 824 may also be used to store an intraoral scan application 850, which may correspond to the similarly named component of FIG. 1. The computer readable storage medium 824 may also store a software library containing methods for an intraoral scan application 850. While the computer-readable storage medium 824 is shown in an example embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium other than a carrier wave that is capable of storing or encoding a set of instructions for execution by the machine and that cause the machine to perform any one or more of the methodologies of the present invention. The term "computer-readable storage medium" shall accordingly be taken to include, but not be limited to, solid-state memories, and optical and magnetic media.

It is to be understood that the above description is intended to be illustrative, and not restrictive. Many other embodiments will be apparent upon reading and understanding the above description. Although embodiments of the present invention have been described with reference to specific example embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense. The scope of the invention should, therefore, be determined with reference to the appended claims, along with the full scope of equivalents to which such claims are entitled.

What is claimed is:

1. A scanning system for performing intraoral scanning and generating a three-dimensional (3D) rendering of one or more dental sites, the scanning system comprising:
   an intraoral scanner configured to capture scan data of the one or more dental sites when operated in a scan mode; and
   a computing device to generate the 3D rendering of the one or more dental sites from the captured scan data of the one or more dental sites and output the 3D rendering to a display;
   wherein the intraoral scanner comprises at least one of a button or a touch sensor to provide manual interaction with the computing device, where:
      a first activation of the at least one of the button or the touch sensor causes the scanning system to enter the scan mode, wherein the 3D rendering has a first visualization during the scan mode;
      a second activation of the at least one of the button or the touch sensor causes the scanning system to enter an inspection mode in which a view of the 3D rendering is adjustable based on movements of the intraoral scanner; and
      a third activation of the at least one of the button or the touch sensor causes the scanning system to enter an overlay mode that is distinct from the inspection mode, wherein the computing device is to present a menu visualized on top of the 3D rendering on the display while the scanning system is in the overlay mode, the menu comprising one or more instructions for use of the intraoral scanner to control a user interface of the scanning system, wherein the 3D rendering has a second visualization during the overlay mode, the second visualization being different from the first visualization, and wherein the intraoral scanner is usable to control the user interface to navigate between scan segments or enter the inspection mode according to the one or more instructions;
   wherein the computing device is to:
      receive, via the intraoral scanner, input associated with one of the presented instructions; and
      perform a function based on the received input.

2. The scanning system of claim 1, wherein the one or more instructions comprise instructions for transitioning to a next segment or a previous segment, and wherein the function is to proceed to a scan of the next segment or to proceed to a scan of the previous segment.

3. The scanning system of claim 1, wherein the one or more instructions comprise at least one of an instruction for proceeding to a next mode or an instruction for repeating or continuing to a previous mode.

4. The scanning system of claim 1, wherein while the scanning system is in the scan mode, the intraoral scanner is to capture scan data of a first dental site of the one or more dental sites and a second dental site of the one or more dental sites, wherein the first dental site comprises a first one of an upper dental arch or a lower dental arch, wherein the second dental site comprises a second one of the upper dental arch or the lower dental arch, and wherein an activation of at least one of the button or the touch sensor causes the scanning system to transition from scanning the first dental site to scanning the second dental site.

5. The scanning system of claim 4, wherein while the scanning system is in the scan mode, a further activation of the at least one of the button or the touch sensor causes the scanning system to transition from scanning the second dental site to scanning a patient bite, wherein the patient bite is to be scanned during closure of a patient's mouth with the intraoral scanner directed towards an interface area of the upper dental arch and the lower dental arch.

6. The scanning system of claim 5, wherein while the scanning system is in the scan mode, a further activation of the at least one of the button or the touch sensor causes the scanning system to transition from scanning the patient bite to scanning a preparation tooth on the upper dental arch or the lower dental arch.

7. The scanning system of claim 1, further comprising:
a motion sensor, wherein the computing device is to translate detected movement of the intraoral scanner measured by the motion sensor into an input command to adjust the view of the 3D rendering of the one or more dental sites based on the input command while in the inspection mode.

8. The scanning system of claim 1, wherein the first activation, the second activation and the third activation are different types of activation that are performed.

9. The scanning system of claim 1, wherein the first activation, the second activation and the third activation each comprise a different one of at least one of an upward swipe gesture, a downward swipe gesture, a leftward swipe gesture, a rightward swipe gesture, a hold gesture, a tap gesture, a circular gesture, or a button press gesture.

10. The scanning system of claim 1, wherein details of the 3D rendering are obscured in the second visualization, and wherein the details are unobscured in the first visualization.

11. The scanning system of claim 1, where the first activation is a first type of activation, where the second activation is a second type of activation, wherein the third activation is a third type of activation, and where:
the first type of activation, the second type of activation, the third type of activation, or a fourth type of activation of the at least one of the button or the touch sensor causes the scanning system to enter an image processing mode;
wherein the computing device is further to perform the following while in the image processing mode:
generate a virtual 3D model of the one or more dental sites; and
output the virtual 3D model of the one or more dental sites to the display.

12. The scanning system of claim 1, wherein a right side and a left side of the intraoral scanner is not fixed, and wherein the computing device is further to:
designate a first side of the intraoral scanner as a left side and a second side of the intraoral scanner as a right side.

13. The scanning system of claim 12, wherein the computing device is further to:
determine an orientation of the intraoral scanner relative to the display based on a configuration, wherein the first side and the second side of the intraoral scanner are designated based on the determined orientation.

14. The scanning system of claim 12, wherein the computing device is further to:
detect an orientation of the intraoral scanner relative to the display, wherein the first side and the second side of the intraoral scanner are designated based on the detected orientation.

15. A scanning system for performing intraoral scanning and generating a three-dimensional (3D) rendering of a dental site, the scanning system comprising:
an intraoral scanner configured to capture scan data of the dental site when operated in a scan mode, the intraoral scanner comprising a motion sensor; and
a computing device to generate the 3D rendering of the dental site from the captured scan data of the dental site and output the 3D rendering to a display;
wherein the intraoral scanner comprises one or more input devices configured to provide manual interaction with the computing device, where:

a first activation of the one or more input devices causes the scanning system to enter the scan mode, wherein the 3D rendering has a first visualization during the scan mode;
a second activation of the one or more input devices causes the scanning system to enter an inspection mode in which a view of the 3D rendering is adjustable based on movements of the intraoral scanner; and
a third activation of the one or more input devices causes the scanning system to enter an overlay mode that is distinct from the inspection mode, wherein the computing device is to present an overlay visualized on top of the 3D rendering of the dental site on the display while the scanning system is in the overlay mode, the overlay comprising instructions for use of the intraoral scanner to execute one or more application control options for controlling an intraoral scan application, wherein the intraoral scanner is usable to implement the application control options based on motion input from the motion sensor, wherein the 3D rendering has a second visualization during the overlay mode, the second visualization being different than the first visualization.

16. The scanning system of claim 15, wherein the overlay comprises at least one of a first option for proceeding to a next segment of the dental site or a second option for returning to a previous segment of the dental site.

17. The scanning system of claim 15, wherein while the scanning system is in the scan mode, the intraoral scanner is to capture scan data of a first segment of the dental site and a second segment of the dental site, wherein the first segment comprises a first one of an upper dental arch or a lower dental arch, and wherein the second segment comprises a second one of the upper dental arch or the lower dental arch, and wherein an activation of the one or more input devices causes the scanning system to transition from scanning the first segment to scanning the second segment.

18. The scanning system of claim 17, wherein while the scanning system is in the scan mode, a further activation of the one or more input devices causes the scanning system to transition from scanning the second segment to scanning a patient bite segment, wherein the patient bite segment is to be scanned during closure of a patient's mouth with the intraoral scanner directed towards an interface area of the upper dental arch and the lower dental arch.

19. The scanning system of claim 15, where:
an activation of the one or more input devices causes a view of the 3D rendering of the dental site to become adjustable, wherein the motion sensor is configured to detect movement of the intraoral scanner, and wherein the computing device is to translate the detected movement of the intraoral scanner into an input command to adjust the view of the 3D rendering of the dental site based on the input command.

20. The scanning system of claim 15, wherein the first activation and the second activation are both performed with a same input device.

21. The scanning system of claim 15, wherein the one or more input devices comprise at least one of a button or a touch sensor.

22. An intraoral scanning system, comprising:
an intraoral scanner configured to capture scan data of an oral cavity, wherein the intraoral scanner comprises one or more buttons and/or touch sensors configured to provide manual interaction with a computing device of the intraoral scanning system; and the computing device, wherein the computing device is to:
receive first scan data of a first segment of the oral cavity from the intraoral scanner;
generate a first three-dimensional (3D) rendering of the first segment of the oral cavity using the first scan data;
output the first 3D rendering to a display, the first 3D rendering having a first visualization;
receive a first activation of at least one button or touch sensor of the one or more buttons and/or touch sensors;
enter an inspection mode responsive to the first activation of the at least one button or touch sensor, wherein a view of the 3D rendering is adjustable based on movements of the intraoral scanner during the inspection mode;
receive a second activation of at least one button or touch sensor of the one or more buttons and/or touch sensors;
enter an overlay mode that is distinct from the inspection mode responsive to the second activation of the at least one button or touch sensor; and
while in the overlay mode, update the first 3D rendering to have a second visualization, the second visualization being different than the first visualization, and present an overlay visualized on top of the first 3D rendering on the display, wherein the overlay comprises instructions for use of the intraoral scanner to transition a scan application to at least one of the inspection mode, a previous segment of the oral cavity or a next segment of the oral cavity using the intraoral scanner.

23. The intraoral scanning system of claim 22, wherein the computing device is further to:
navigate to the next segment based on an input from the intraoral scanner;
receive second scan data of the next segment of the oral cavity from the intraoral scanner;
generate a second 3D rendering of the next segment using the second scan data; and
output the second 3D rendering to the display.

24. The intraoral scanning system of claim 22, wherein the intraoral scanning system is to operate in a scan mode during receipt of the first scan data, wherein a third activation of the one or more buttons and/or touch sensors causes the intraoral scanning system to enter the scan mode, and wherein the second activation of the one or more buttons and/or touch sensors causes the intraoral scanning system to enter the overlay mode from the scan mode, wherein the overlay is output to the display while the intraoral scanning system is in the overlay mode, and wherein the overlay is not output to the display while the intraoral scanning system is in the scan mode.

25. The intraoral scanning system of claim 22, wherein the intraoral scanner comprises at least one motion sensor configured to detect movement of the intraoral scanner, and wherein the computing device is to translate the detected movement of the intraoral scanner into an input command and to adjust the view of the first 3D rendering based on the input command during the inspection mode.

26. The intraoral scanning system of claim 22, wherein the first segment and the next segment are each a different one of an upper dental arch segment, a lower dental arch segment, a bite segment, or a preparation tooth segment.

27. An intraoral scanning system, comprising:
an intraoral scanner configured to capture scan data of an oral cavity, wherein the intraoral scanner comprises one or more buttons and/or touch sensors configured to provide manual interaction with a computing device of the intraoral scanning system; and
the computing device, wherein the computing device is to:
receive an input based on an activation of at least one button or touch sensor of the one or more buttons and/or touch sensors included in the intraoral scanner;
determine, based on the activation of the at least one button or touch sensor of the one or more buttons and/or touch sensors included in the intraoral scanner and on a current mode of the intraoral scanning system, a first function to perform; and
perform the first function, wherein the first function comprises an overlay mode that changes a visualization of a 3D surface of a dental site output to a display by obscuring the 3D surface of the dental site and outputs an overlay to the display, wherein the overlay comprises instructions for use of the intraoral scanner to control a user interface of the intraoral scanning system, the instructions comprising options for transitioning at least one of a) between modes of the intraoral scanning system, b) between scan segments, or c) to an inspection mode;
receive a second input associated with the instructions based on a second activation of the one or more buttons and/or touch sensors included in the intraoral scanner;
enter the inspection mode, wherein a view of the 3D surface is adjustable based on movements of the intraoral scanner during the inspection mode;
receive a third input associated with one of the instructions based on a third activation of the one or more buttons and/or touch sensors included in the intraoral scanner;
determine, based on the third activation of the one or more buttons and/or touch sensors included in the intraoral scanner and on the current mode of the intraoral scanning system, a second function to perform; and
perform the second function, wherein the second function comprises one of transitioning to a next mode, transitioning to a previous mode, transitioning to a next scan segment, or transitioning to a previous scan segment.

28. The intraoral scanning system of claim 27, wherein the computing device is further to:
receive motion data from at least one motion sensor of the intraoral scanner while in the inspection mode;
translate the motion data into an input command to adjust a view of the 3D surface; and
adjust the view of the 3D surface based on the input command.

29. The intraoral scanning system of claim 27, wherein the second function is a function to transition the intraoral scanning system from a current scan segment to the next scan segment, wherein the current scan segment and the next scan segment are each a different one of an upper dental arch segment, a lower dental arch segment, a bite segment, or a preparation tooth segment.

* * * * *